US011433212B1

(12) United States Patent
Hafeman et al.

(10) Patent No.: US 11,433,212 B1
(45) Date of Patent: Sep. 6, 2022

(54) SELF-CONTAINED FACE MASK SYSTEM WITH AUTOMATIC DROPLET DISPENSER FOR HUMIDIFICATION

(71) Applicant: Health Micro Devices Corporation, Greenleaf, WI (US)

(72) Inventors: Dean Hafeman, Greenleaf, WI (US); Seongsik Chang, Santa Clara, CA (US)

(73) Assignee: Health Micro Devices Corporation, Greenleaf, WI (US)

(*) Notice: Subject to any disclaimer, the term of this patent is extended or adjusted under 35 U.S.C. 154(b) by 0 days.

(21) Appl. No.: 17/496,663

(22) Filed: Oct. 7, 2021

(51) Int. Cl.
*A61M 16/06* (2006.01)
*A61M 16/10* (2006.01)
(Continued)

(52) U.S. Cl.
CPC .... *A61M 16/1075* (2013.01); *A61M 16/0006* (2014.02); *A61M 16/06* (2013.01);
(Continued)

(58) Field of Classification Search
CPC ............ A41D 13/11; A61B 2560/0247; A61B 46/00; A61B 5/0205; A61B 5/021; A61B 5/024; A61B 5/02438; A61B 5/05; A61B 5/0816; A61B 5/14546; A61B 5/1455; A61B 6/00; A61B 6/507; A61B 8/00; A61B 8/02; A61B 8/04; A61B 8/06; A61H 1/00; A61H 2201/1238; A61H 2201/5025; A61H 2205/023; A61H 2205/027; A61H 23/02; A61H 23/04; A61J 2200/74; A61J 3/00; A61K 9/20; A61K 9/2072; A61K 9/209; A61K 9/2095; A61K 9/70; A61L 24/00; A61L 24/04; A61L 24/06; A61L 31/04; A61L 31/06; A61M 15/00; A61M 16/00;
(Continued)

(56) References Cited

U.S. PATENT DOCUMENTS

| | | |
|---|---|---|
| 3,965,376 A | 6/1976 | Arndt |
| 4,296,421 A | 10/1981 | Hara et al. |

(Continued)

OTHER PUBLICATIONS

Ermer, et al. "Comparison of 7 Different Sensors for Detecting Low Respiratory Rates Using a Single Breath Detection Algorithm in Nonintubated, Sedated Volunteers," Technology, Computing, and Simulation, vol. 129, No. 2, Aug. 2019, pp. 399-408.

(Continued)

*Primary Examiner* — Annette Dixon
(74) *Attorney, Agent, or Firm* — Perkins Coie LLP

(57) ABSTRACT

Introduced here is a face mask system having a mask enclosure that contains, or otherwise directly supports, an automated liquid-droplet dispensing mechanism (ADM) for humidification. In operation, the enclosure and ADM are compact and lightweight so that when worn by a user can be supported entirely by the user's head and neck. The enclosure can be comprised of one or more layers of breathable fabric adapted to flexibly conform to the face of a user when worn and form a cavity that is adjacent to the user's nostrils and mouth. The ADM can be comprised of a reservoir in which liquid is stored, a respiratory cycle detector, a timer and controller, and a droplet dispenser that controllably dispenses droplets of the liquid from the reservoir into the cavity for inhalation by the user.

26 Claims, 11 Drawing Sheets

(51) Int. Cl.
*A61M 16/00* (2006.01)
*A61M 16/20* (2006.01)
*A61M 16/16* (2006.01)

(52) U.S. Cl.
CPC .......... *A61M 16/16* (2013.01); *A61M 16/205* (2014.02); *A61M 2016/0018* (2013.01); *A61M 2205/0294* (2013.01); *A61M 2205/3327* (2013.01); *A61M 2205/3368* (2013.01); *A61M 2230/42* (2013.01)

(58) Field of Classification Search
CPC ................ A61M 16/024; A61M 16/06; A61M 16/107; A61M 16/16; A61M 16/20; A61M 16/208; A61M 2016/0021; A61M 2016/0027; A61M 2016/0033; A61M 2016/0039; A61M 2202/0007; A61M 2202/0208; A61M 2202/0216; A61M 2202/0225; A61M 2202/0266; A61M 2202/064; A61M 2205/332; A61M 2205/3334; A61M 2205/3365; A61M 2205/3375; A61M 2205/42; A61M 2205/50; A61M 2205/502; A61M 2205/505; A61M 2205/581; A61M 2205/582; A61M 2205/583; A61M 2205/59; A61M 2205/8206; A61M 2210/0618; A61M 2210/0662; A61M 2210/0681; A62B 18/00; A62B 18/02; A62B 23/02; A62B 7/14; A62B 9/02; B41J 2/04; B41J 2/175; B41J 3/407; H01L 31/16
See application file for complete search history.

(56) References Cited

U.S. PATENT DOCUMENTS

| | | | |
|---|---|---|---|
| 4,490,728 A | 12/1984 | Vaught et al. | |
| 4,509,062 A | 4/1985 | Low et al. | |
| 4,929,963 A | 5/1990 | Balazar | |
| 5,758,637 A | 6/1998 | Ivri et al. | |
| 5,825,386 A | 10/1998 | Ohashi | |
| 5,855,208 A * | 1/1999 | Askill | A61L 24/06 128/849 |
| 5,938,117 A | 8/1999 | Ivri | |
| 5,946,012 A | 8/1999 | Courian et al. | |
| 6,192,876 B1 * | 2/2001 | Denyer | A61B 5/087 128/204.18 |
| 7,111,626 B2 * | 9/2006 | Schmehl | A61D 7/04 128/200.23 |
| 2004/0173147 A1 * | 9/2004 | Figueroa | B41J 2/17513 118/325 |
| 2012/0197093 A1 * | 8/2012 | LeBoeuf | A61B 5/026 600/301 |
| 2013/0255678 A1 * | 10/2013 | Gumaste | A61M 15/0065 128/203.15 |
| 2016/0074618 A1 * | 3/2016 | Foote | F16K 3/03 128/204.23 |
| 2018/0185595 A1 * | 7/2018 | Bogan | A61M 16/06 |
| 2020/0376305 A1 * | 12/2020 | Lang | A62B 18/025 |

OTHER PUBLICATIONS

Carvalho, et al. "The function and performance of aqueous aerosol devices for inhalation therapy," Journal of Pharmacy and Pharmacology, 68, 2016, pp. 556-578.
MAX17291 "High-Voltage, 1A Micropower Boost Converter with Short-Circuit Protection and True Shutdown," 19-100778; Rev 2; Nov. 2020, 21 pages.

* cited by examiner

SELF-CONTAINED FACE MASK SYSTEM WITH AUTOMATIC DROPLET DISPENSER FOR HUMIDIFICATION

TECHNICAL FIELD

Various embodiments relate to the field of healthcare devices and, more particularly, to the fields of liquid spray and atomization of inhaled liquids, finding utility in humidification and misting of aerosols and dispensing of medical treatments by route of inhalation.

BACKGROUND

Many civilizations, ethnic groups, and regional inhabitants, including the Romans, Germans, Japanese, Turks, and Swedes, have long recognized the healthy properties of elevated humidity provided by communal hot baths, hot springs, and steam saunas. It is also a well-known fact, since at least the time of Hippocrates 2,400 years ago, that infectious diseases occur seasonally. Different diseases occur at completely different times of the year. Those caused by respiratory viruses, like the seasonal flu, respiratory synclinal virus, or the Severe Acute Respiratory Syndrome (SARS) viruses, are strongly correlated with seasons of low absolute humidity, particularly the dry air of the winter months (J. Cohen, *Science*, 36, 1294-1297, 2020 and J. Shaman, E Goldstein, & M. Lipsitch, *Amer. J. Epidem.* 173, 127-135, 2011.)

The mechanisms for increased transmission of respiratory viruses in dry environments are incompletely understood, but it is recognized generally that dehydration leaves the respiratory airways more susceptible to infectious agents, particularly to viral infectious agents, such as the flu or the SARS viruses. For example, certain genetic traits, such as those occurring in cystic fibrosis, result in depletion in the volume of airway surface liquid (ASL) that bathes the surface of epithelial cells that line the respiratory tract. The reduction in ASL volume results in an increase in viscosity that impairs mucus clearance from the lungs that leads to chronic airway infections.

Humidistat and humidifier devices help to maintain the humidity in heated buildings. Providing optimal and consistent humidity, however, remains a substantial problem in many human environments, particularly in refrigerated or air-conditioned buildings. The problems are most acute in cold-room or freezer workplaces that render the air in those environments very dry. Facilities such as cold storage or meat-packing plants, where workers are in close proximity, frequently are focal points for the transmission of respiratory infections. At present, there are no convenient or practical means for such workers to maintain optimal hydration of their respiratory tracts while working in such dry environments.

Similarly, airline passengers and crew are exposed to very dry air over many hours particularly during long transcontinental or international flights. The relative humidity levels within airline cabins, while in flight, generally are quite low because of the very cold air present at normal flight altitudes (e.g., more than 30,000 feet above sea level). This extremely dry air is compressed and used to provide fresh air within airline cabins during normal airline flights. The low humidity generally leads to an unhealthy condition within airplane cabins that similarly is conducive to the spread of respiratory diseases.

Increasing the humidity of entire airplane cabins would improve the respiratory health of passengers and crew and likely would decrease the spreading of respiratory bacterial and viral infections. A substantial fraction of water vapor, added to airline cabins, however, would condense on the cold, peripheral structural elements of the airplane cabin causing shorting and corrosion problems with wiring, as well as increasing structural corrosion.

Therefore, despite a great need, there are no practical or convenient means within the prior art for providing optimal humidity to those individuals that need to maintain their mobility while situated in cold or dry environments. Particularly needed is a practical and convenient way to introduce sustained humidity to the upper respiratory tract, including the nasal passages, nasal sinuses, nasopharynx, and pharynx. These are the portions of the upper respiratory tract are the first targets of a respiratory virus entering the respiratory airway, and thus their maintenance is critical to prevention of respiratory infections.

Small, hand-held inhaler devices filled with an aqueous liquid are widely available and could be carried into workplaces and aboard airplanes, trains, cars, and the like. Such inhalers, however, require the user continually to coordinate hand-pump compressions with the inhalation phase (also referred to as the "inhalation segment") of the breathing cycle (also referred to as the "respiratory cycle") during use. Because inhaler operation consumes the sustained attention of the user, it is impractical and inconvenient to perform over extended periods of time. Also, inhalers supply humidity solely through the mouth. Inhalers do not supply adequate humidity to the nasal passages and the other outermost regions of the upper respiratory tract that are critical sites for respiratory infections.

External nebulizer devices also can be used to generate aerosols that can be pumped into the nasal passages. Motor-driven fans and pumps commonly are used to drive the aerosols through tubing that connects such external nebulizer devices to the respiratory tracts of users. The aerosols may be delivered into the mouth, or into the nose by employing a nasal mask that is usually formed from solid plastic material with venting holes for exhaust. Such external nebulizer devices generally have large external reservoirs, compressors, pumps, and connecting tubing, however, and therefore are cumbersome and inconvenient to use while working or travelling (e.g., in an airplane). Also, the solid masks of such nebulizer devices generally are uncomfortable to use for extended periods of time.

Small, hand-held, external nebulizer devices that do not have connecting tubing are also available to use for humidification of the environment. However, such hand-held nebulizer devices either require an external supporting structure or need to be held continuously by the user. Such hand-held nebulizer devices also have the disadvantage that the stream of dispensed droplets is not well defined. Consequently, a large excess of droplets must be dispensed because only a small fraction actually enters the nasal passages of the immediate user. Moreover, the inefficient use of liquid in hand-held nebulizer devices causes them to run dry after a few minutes of use, requiring frequent re-filling. These hand-held nebulizer devices also require frequent battery-recharging (because of high, uncontrolled, liquid dispense rates) during continuous use, making them inconvenient to use for extended periods of time. Also, the excess of dispensed droplets has a significant effect on the local environment of the users. For example, neighboring passengers in enclosed spaces (e.g., within airline cabins) may be subjected to the overflow of dispensed droplets, and this can be problematic.

Several chronic disease states also are induced or heightened by lack of humidity in the environment in the upper respiratory tract. One example of such a chronic disease state is inherited cystic fibrosis that results in depletion of the ASL volume and increases mucus viscosity. Periodic treatments for cystic fibrosis, such as hypertonic solutions delivered by inhalers or nebulizers, are beneficial for increasing ASL volume and decreasing mucus viscosity. Without continuous attachment to such an inhaler or nebulizer device, however, there are no convenient means to deliver supplemental liquids to the respiratory airways of cystic fibrosis subjects continuously over longer periods of time (e.g., several hours). Despite a great need, no practical or convenient means exist for providing optimal respiratory humidity to those with chronic diseases that desire free mobility during extended treatment periods.

Figure 1A:
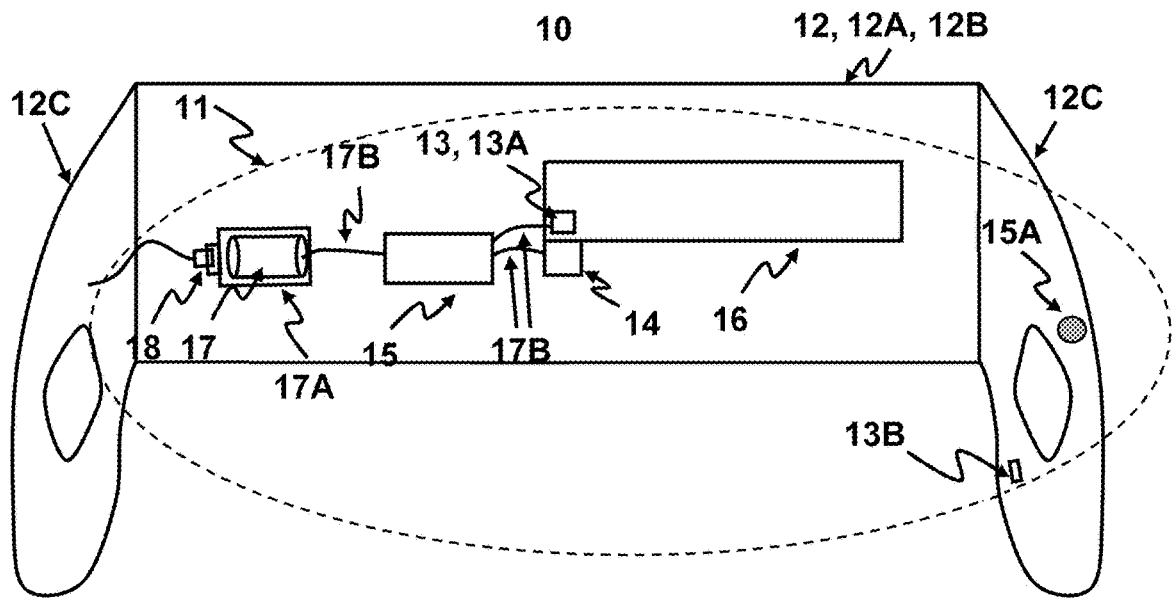
FIG. 1A is a rear view of a face mask system that includes a face mask enclosure comprised of fabric materials and components of a self-contained automated liquid-droplet dispensing mechanism (ADM), shown in schematic form in accordance with various embodiments.

Embodiments are illustrated by way of example and not limitation in the drawings. While the drawings depict various embodiments for the purpose of illustration, those skilled in the art will recognize that alternative embodiments may be employed without departing from the principles of the technology. Accordingly, while specific embodiments are shown in the drawings, the technology is amenable to various modifications.

DETAILED DESCRIPTION OF THE INVENTION

The present disclosure concerns various embodiments of a face mask system comprised of an automated liquid-droplet dispensing mechanism (ADM) that can be integrated together with an enclosure to function as "smart humidifier" that can be worn and supported entirely by the head and neck of the user (also referred to as the "wearer" of the face mask system). The face mask system conveniently provides for continuous humidification where mobility of the user is of paramount importance. The ADM additionally serves to minimize water vapor exhaled by the user of the face mask system so that environmental effects are reduced. The technology described herein provides a practical solution to the problem of humidification of the upper respiratory airways for individuals situated in dry environments, like airline passengers and crew, and for other individuals needing a practical way to increase the humidity of the ambient environment.

As further discussed below, the "smart humidifier" can be comprised of a group of elements that cooperate to perform the needed humidifier functions when combined into a self-contained face mask system that may be lightweight (e.g., less than 100 grams in total), and therefore can be supported comfortably by the head and neck of the user. The ADM at the core of the face mask system can controllably increase the humidity of air that is drawn into the nostrils or mouth as the user inhales air from the face mask system. The ADM includes (i) a liquid reservoir (or simply "reservoir") that may be, for example, a detachable and replaceable cartridge assembly in which liquid is stored, (ii) a droplet generator that is in fluid communication with the reservoir, (iii) a respiratory cycle detector that monitors the "respiratory cycle" or "breathing cycle" of the user, (iv) an electronic timer and controller device (or simply "controller") that is in electronic communication with the respiratory cycle detector and the droplet generator, (v) a user-interactive timer and controller switch and adjustment device, (vi) an internal power source such as a rechargeable battery, or any combination thereof. All components of the ADM can be contained within, or on the surface of, a face mask enclosure that, during operation, is worn and supported entirely by the head and neck of the user.

The ADM of the present disclosure provides for dispensing, from a self-contained reservoir of liquid, either (i) a short pulse of multiple droplets that are ejected simultaneously or (ii) a sequence of individual droplets that are ejected one at a time. The onset of each dispensing pulse or sequence may begin at a predetermined time point with respect to phases of the user's respiratory cycle, principally the time at which exhalation stops and inhalation begins. Said another way, liquid may be dispensed from the reservoir when the exhalation phase of the breathing cycle ends and when the inhalation phase of the breathing cycle begins. In various embodiments either the rate of droplet dispensing or the duration of the dispensing pulse or sequence (i.e., the dispense period) can be adjusted, for example, based on a characteristic of the user (e.g., desired humidity, average length of inhalation phase, etc.), but may be within predetermined upper and lower bounds to provide adequate humidity to maintain the airway surface liquid (ASL) volume and viscosity—especially of the upper respiratory tract—without providing excess moisture. Thereby, the ADM provides for hydration of the ASL of the upper respiratory tract of the user, while also conserving the total amount of liquid consumed from the reservoir. In this way both the volume and the weight of the reservoir can be minimized to allow for integration of the ADM into, or onto the surface of, the protective face mask enclosure, while still providing for several hours of the droplet dispensing. The self-contained face mask system, comprising the ADM and other elements as further discussed below, thereby provides a convenient and practical solution to the humidification problem that plagues individuals that desire to increase humidification of their respiratory airways, while also desiring to maintain relatively unconstrained mobility and freedom to perform other tasks.

In a preferred embodiment, the enclosure of the self-contained face mask system, when worn, will conform to the face of the user to form a primary cavity between the enclosure and the nose and mouth of the user. The primary cavity accommodates one or more components of the ADM and supports their function. In a further preferred embodiment, the enclosure can be comprised of one or more layers of breathable, protective fabric that are adapted to conform flexibly to the face of the user when worn to form the primary cavity. Advantageously, the breathable, protective fabric may form an enclosure that meets the protective face mask requirements of airlines, airports, workplaces, schools, and the like for minimizing the dissemination of respiratory particles in such facilities. Accordingly, the face mask system of the present disclosure can provide the humidity needed for protection of the respiratory airway epithelial cells that are targets of pathogenic bacteria and viruses, while at the same time can reduce the spread of respiratory bacteria and viruses from person to person.

As mentioned above, the ADM within the protective face mask enclosure can include a reservoir in which liquid is stored prior to dispersal as droplets into a primary cavity that is formed between the face mask enclosure of the system and the nose and mouth of the user. The liquid may be pure water, or the liquid may be an aqueous solution of protective electrolyte substances. Liquid may be supplied together with a refillable cartridge assembly that is detachably connectable to and from the self-contained face mask system, or the liquid may be supplied as a reservoir-refilling kit. In embodiments where the reservoir is designed to be refilled periodically with liquid, the reservoir may be attached fixedly to the enclosure of the self-contained face mask system.

The face mask system of the present disclosure may find utility in settings other than in dry workplace environments or within airline cabins, by providing humidity, electrolytes, and other medications that are advantageous for treating chronic respiratory conditions currently without convenient means to supply such substances to the respiratory tract over extended periods of time, including several hours of use.

For the purpose of illustration, embodiments of the ADM contained within the face mask system may be described in the context of instructions that are executable by a controller, which may be a microcontroller, microprocessor, or some other form of central processing unit (also referred to as a "processor"). For example, executable instructions for controlled dispensation of liquid in the form of droplets may be stored, either as firmware or software, in a memory of the controller and when executed by the controller the instructions may cause the controller to (i) examine measurements generated by a sensor that are indicative of a characteristic of air exhaled through the nostrils or mouth by a user, (ii) generate a signal in response to determining, in real time based on analysis of the measurements, that an exhalation phase has ended, and (iii) transmit the signal to a droplet generator so as to commence a dispensation operation in which liquid droplets are dispensed generally toward the nostrils of the user. Thereafter, the controller may generate a second signal in response to determining, in real time based on analysis of the measurements, that peak inhalation has been achieved. The controller may transmit the second signal to the droplet generator so as to conclude the dispensation operation. Alternatively, the controller may transmit the second signal to the droplet generator after a predetermined amount of time has elapsed as further discussed below. Those skilled in the art will recognize that aspects of the technology could be implemented via discrete logic components (e.g., transistor logic circuits) instead of, or in addition to, firmware or software stored in memory. The principal advantages of storing instructions in a memory (e.g., in the form of firmware or software) can be the convenience and ease at which the instructions can be updated or modified. Particularly advantageous may be operations of an associated processor that modify the stored instructions, or accumulated data, in real time, so as to minimize input noise from environmental sensors comprising the ADM or otherwise improve the droplet-dispensing characteristics of the face mask system.

Terminology

Brief definitions of terms, abbreviations, and phrases used throughout the present disclosure are given below.

The terms "connected," "coupled," and variants thereof are intended to include any connection or coupling between two or more elements, either direct or indirect. The connection or coupling can be physical, logical, or a combination thereof. For example, elements may be electrically or communicatively connected to one another despite not sharing a physical connection.

The terms "electronic timer and controller mechanism," "timer and controller," and "controller" broadly refer to components implemented via software, firmware, or hardware that are operable to control elements of the self-contained system. Examples of "controllers" include general-purpose processors and application-specific integrated circuits (ASICs).

The term "about" means to within ±10 percent of the recited value. The terms "roughly" and "significant" refer to within ±25 percent of the recited value, or to within ±25 percent of the maximum value over a recited time interval, respectively.

Overview of Self-Contained Face Mask System Introduced above, and described in further detail below, is a self-contained mask system with an automated liquid-droplet dispensing mechanism (ADM) for controlled humidification of inhaled air. The self-contained face mask system (or simply "system") can include a protective face mask enclosure that is comprised of one or more layers of breathable fabric that are adapted to flexibly conform to the face, when worn by a user to form a primary cavity that is adjacent to the nostrils and mouth of the user of the system. The protective face mask enclosure supports the entire ADM that controllably dispenses droplets of the liquid into the primary cavity for inhalation by the user. Thereby, the face mask system, when light in weight (e.g., less than 100 grams) can be supported entirely by the head and neck of the user while providing for controlled humidification of inhaled air.

The ADM includes several components that are able to work in concert to dispense the droplets of liquid in a controlled fashion. For example, the ADM may include (i) a sensor configured to generate measurements that are representative of a characteristic of air that is exhaled through the nostrils or mouth of the user, (ii) a controller configured to generate a signal in response to determining in real time, based on analysis of the measurements, that an exhalation phase has ended, and (iii) a droplet generator configured to initiate, in response to receiving the signal from the controller, dispensation of liquid from the reservoir into the primary cavity in the form of droplets. Normally, droplet dispensing begins roughly when the inhalation phase commences, so as to humidify air drawn into the nostrils or mouth during the inhalation phase of a breathing cycle (also called a "respiratory cycle"). Moreover, dispensation may end before the inhalation phase concludes, such that the resulting dispense period occurs over only an initial portion of the inhalation phase. Dispensation of droplets only over an initial portion of the inhalation phase helps to ensure that significant numbers of droplets do not remain in the primary cavity following the inhalation phase of a breathing cycle.

At a high level, the sensor is responsible for monitoring a characteristic of air that is exhaled through the nostrils or mouth of the user, either directly or indirectly, so that the controller can monitor the entire breathing cycle. The sensor can take several different forms, however. As an example, the sensor may be an accelerometer that is connected to a flap situated in an exhaust valve in the breathable fabric of the enclosure. In such embodiments, the accelerometer measures motion of the flap, and this motion can be used as an indicator of whether air is being inhaled or exhaled through the nostrils or mouth of the user. As another example, the sensor may be an accelerometer that is mounted to a flexible membrane or substrate embedded into an aperture in the breathable fabric of the mask. In such embodiments, the accelerometer, when attached to the flexible membrane or substrate, can generate measurements that are indicative of motion of the flexible membrane or substrate, and this motion can be used as an indicator of whether air presently is being inhaled or exhaled through the nostrils or mouth of the user. As another example, the sensor may be a temperature sensor that is located along an interior surface of the mask and within the primary cavity. In such embodiments, the temperature sensor can generate measurements that are indicative of the air temperature changes inside the cavity, and these temperatures can be used as an indicator of whether air presently is being inhaled or exhaled through the nostrils or mouth of the user.

The droplet generator also can take several different forms. As an example, the droplet generator may include a vibrating mesh nebulizer (VMN) disc that is operable to induce dispensation of droplets through ultrasonic vibration. Normally, a VMN disc includes (i) a plate with a first side that has one or more ingress holes through which liquid is able to enter the plate and a second side that has one or more egress holes through which the liquid is able to exist the plate and (ii) a vibration element configured to induce movement of the liquid through the plate by ultrasonic vibration. While the ingress hole(s) on the first side of the plate may be fluidly connected to the egress hole(s) on the second side of the plate, these holes do not need to be fluidly connected to one another in a one-to-one relationship. A single ingress hole may be fluidly connected to multiple egress holes (e.g., tens or hundreds) to facilitate dispensation of small droplets. As another example, the droplet generator may include an array of piezoelectric actuators, each of which may have (i) a chamber in which liquid is contained, (ii) a nozzle, and (iii) a piezoelectric element that is configured to displace the liquid in the chamber when a suitable voltage is applied thereto, thereby causing the liquid to be dispensed through the nozzle in the form of a droplet. As another example, the droplet generator may include an array of thermal actuators, each of which may have (i) a chamber in which liquid is contained, (ii) a nozzle, and (iii) a heating element that is configured to heat the liquid to boiling, thereby causing a bubble to form that forces the liquid to be dispensed through the nozzle in the form of a droplet.

Figure 1B:
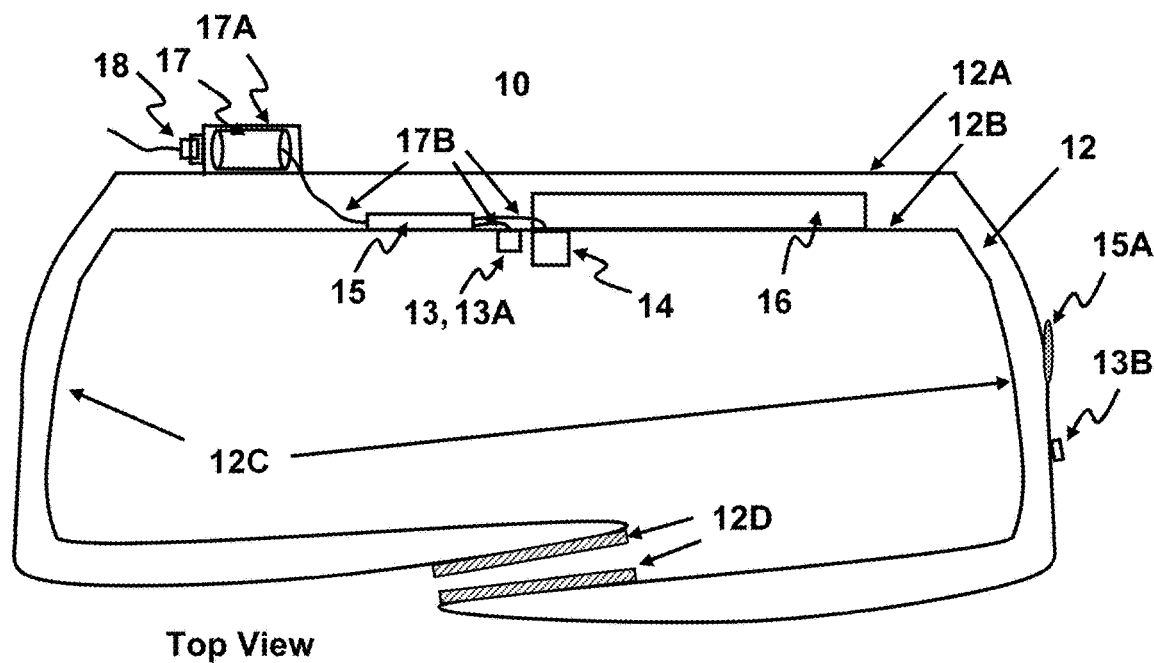
FIG. 1B is a top-view of the face mask system showing the components of the ADM and their possible placements within, on, or between the layers of face mask materials.
Figure 1C:
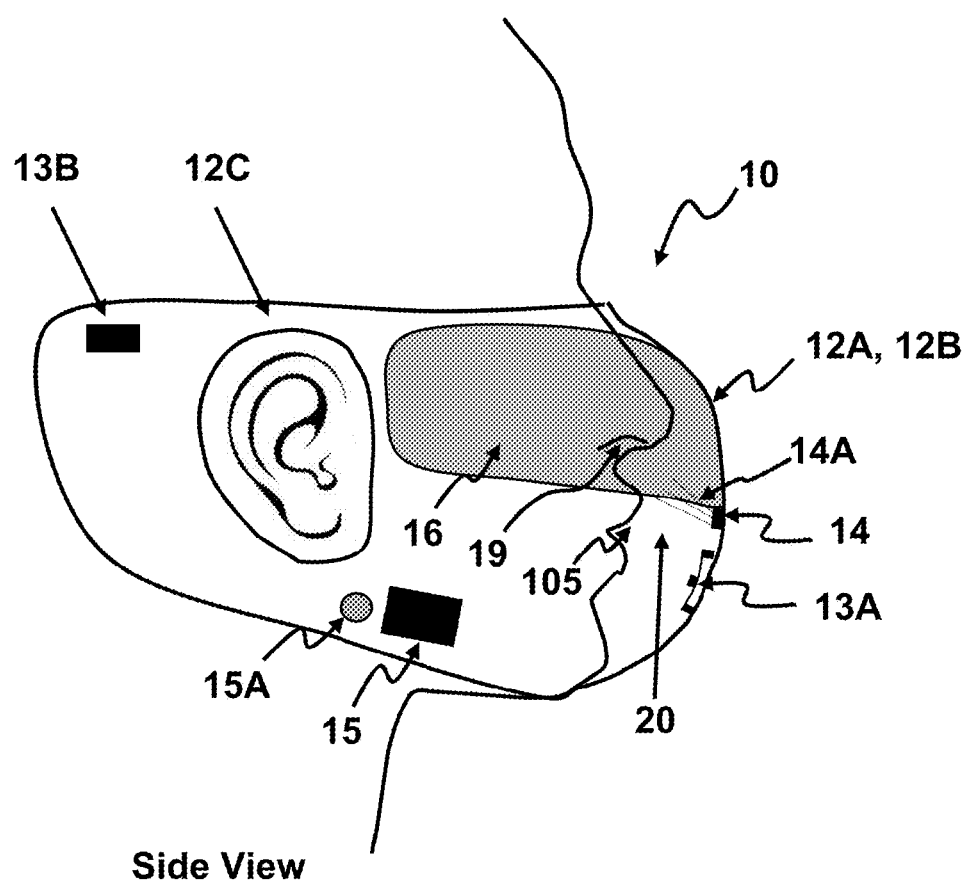
FIG. 1C is a side view of the face mask system showing placement of the components of the ADM with respect to the face of a user of the face mask system. Also shown is a preferred dispensation path of liquid droplets that travel from a droplet generator of the ADM, through a primary cavity formed between the face mask enclosure and the nose and mouth of the user, and into the nasal passages of the user.
Figure 2:
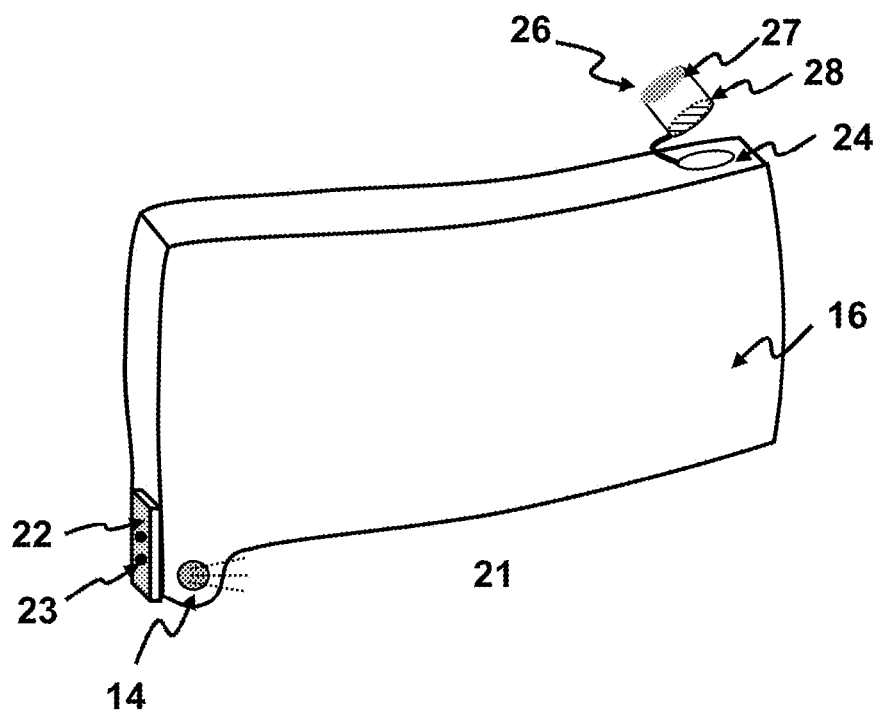
FIG. 2 illustrates how the droplet generator of the ADM can be combined with a reservoir of the ADM to form a cartridge assembly in some embodiments.

FIGS. 1A, 1B, and 1C show a self-contained face mask system 10 that includes a collection of elements or components that form an ADM 11 that substantially is disposed on, or enclosed within, a face mask enclosure 12. The enclosure 12 comprises lining material that in some embodiments is made of two or more layers of breathable fabric comprising an outermost layer 12A and an innermost layer 12B. In embodiments where the enclosure includes more than one layer of fabric, the fabric layers may be comprised of the same, or different, materials. Examples of suitable materials include cotton, wool, silk, cellulose, nylon, rayon, polypropylene, and the like. Regardless of the number of layers, the fabric materials generally may be tightly woven, and free of apertures open to the environment, so that droplets emitted by the ADM 11, as described above and subsequently, are not able to escape readily into the ambient environment prior to inhalation by the user.

As shown in FIG. 1C, when the face mask system 10 is worn by a user, a primary cavity 20 is formed between the innermost layer 12B of fabric, the mouth 105, and the nostrils 19 that form openings to the nasal passages of the user. The primary cavity 20 may be continuously open and unblocked along a preferred direct path 14A between a droplet generator 14 of the ADM 11 and the nostrils 19 and mouth of the mask user so that any droplets that are dispensed can readily be inhaled by the user. The ADM 11 additionally can include a respiratory cycle detector 13, a timer and controller 15, a user-interactive on/off switch that also serves as a timer and controller adjustment device 15A, a liquid reservoir 16, a retainer or attachment provision 17A (also called the "holder") for fixedly attaching a power source 17 to the enclosure 12, and one or more conductive elements 17B for distribution of power to and electrical communication between the electronic timer and controller, the respiratory cycle detector, and the droplet generator. The ADM also may have a power charging connection 18 for charging a battery when one or more rechargeable batteries may be inserted into the holder, to provide a power source.

The respiratory cycle detector 13 can detect and monitor the flow of air inhaled into, or exhaled out of, the respiratory airways of the mask user. For this purpose, the respiratory cycle detector 13 will have at least one sensor 13A that is configured to generate measurements that are representative of a characteristic of air that is exhaled through the nostrils or mouth of the user. The measurements may indicate one or more temporal parameters, including the time ($T_1$) at which the respiratory cycle of the user changes from an exhalation phase to an inhalation phase, the time ($T_2$) during the inhalation phase immediately following $T_1$ at which the rate of change in volumetric flow rate is maximal, and time ($T_3$) during the inhalation phase at which the respiratory cycle of the user changes from the inhalation phase to an exhalation phase.

The timer and controller 15 can be configured to generate a dispense "start" signal at $T_1$, in response to determining, in real time based on analysis of the measurements generated by respiratory cycle detector 13, that an exhalation phase has ended and an inhalation phase has begun. As mentioned above, the ADM 11 also includes a droplet generator 14 that can be configured to dispense droplets of liquid from the reservoir 16 where the individual droplets are exceedingly small so as not to exceed 1 nanoliter in volume. In response to receiving the dispense "start" signal from the timer and controller 15, the droplet generator 14 may initiate droplet dispensation for a period (generally called the dispense period) that coincides with the inhalation phase to humidify air drawn into the nostrils or mouth during the inhalation phase. Moreover, dispensation may end before the inhalation phase concludes, such that dispensation occurs over only an initial portion of the inhalation phase. To do this, a dispense "end" signal can be sent by timer and controller 15 at ($T_2+y$) to droplet generator 14 in response to determining, in real time based on analysis of the measurements generated by respiratory cycle detector 13, that the rate of change in volumetric flow rate, during the inhalation phase of the respiratory cycle, is maximal. Generally, the dispense "end" signal is sent by timer and controller 15 to droplet generator 14 after an adjustable delay time y that allows the user to either increase or decrease the dispense period over which droplets are dispensed during each inhalation phase.

When the face mask system 10 is switched on by the user, for example by pressing a button on, or rotating, the user-interactive on/off switch (that also serves as a timer and controller adjustment device 15A), the default delay time may be zero. The delay time y may be adjusted by the user by interacting with the timer and controller adjustment device 15A that is attached to the outermost layer 12A of fabric of the face mask system 10, as shown in FIGS. 1A, 1B, and 1C. The timer and controller adjustment device 15A could take on the form of an adjustment knob that can be turned by the user to adjust the duration of the dispense period. The value of the delay time y may be adjustable, for example, between −0.5 and +0.5 seconds. In some embodiments, however, the delay time y is a function of $T_1$ and $T_2$. For example, the delay time may be determined dynamically (i.e., in real time) by timer and controller 15 as follows:

$$y=x(T_2-T_1), \quad \text{Eq. 1}$$

where the value of x will generally be between −0.9 and +1.5, though the default value of x may be zero. If the user desires to increase the amount of liquid dispensed, the user can interact with timer and controller adjustment device 15A in one way (e.g., by turning the adjustment knob clockwise) to either increase x by a predetermined amount (e.g., 0.1) or increase the delay time y by a predetermined amount (e.g., 0.1 seconds). Regardless of the preselected delay parameter settings selected by the user, the timer and controller 15 may send a mandatory dispense "end" signal to droplet generator 14 upon receiving information from respiratory cycle detector 13 that time $T_3$ has arrived. In this way, regardless of any preset delay time delays selected by the user, no dispensing may occur during the exhalation phase of a respiratory cycle.

If the user desires to decrease the amount of liquid dispensed, the user can interact with the timer and controller adjustment device 15A in another way (e.g., by turning the adjustment knob counter-clockwise) to either decrease x by a predetermined amount (e.g., 0.1) or decrease the delay time y by a predetermined amount (e.g., 0.1 seconds). To perform such reductions in dispense time, it may be necessary for timer and controller 15 to send a dispense "end" signal to droplet generator 14 before receiving information from respiratory cycle detector 13, that the time $T_2$ has been achieved. For this purpose, timer and controller 15 may store a running average M of ($T_2-T_1$) values. For example, timer and controller 15 may store a collection of data (e.g., 5 or 10) of the most recent ($T_2-T_1$) values, or timer and controller 15 may store the ($T_2-T_1$) values corresponding to a certain interval of time (e.g., the preceding 5, 10, or 30 minutes). In this way, upon beginning the next inhalation phase, timer and controller 15 can send a dispense "start" signal to droplet generator 14 at $T_1$ (the same as the default condition). Next, however, timer and controller 15 may send a dispense "end" signal to droplet generator 14 at an imputed time $T_2'$ that is calculated from the previous running average M and the new delay setting preselected by the user. For example, if the user selects a 0.4 reduction in x from the default condition (e.g., by turning timer and controller adjustment device 15A counter-clockwise four "clicks") and the running average M of the most recent ($T_2-T_1$) values is 0.5 seconds, then the applied change in delay time y=−0.4 (0.5 seconds)=−0.2 seconds. In this case, the timer and controller 15 will send a dispense "end" signal 0.3 seconds after $T_1$, that is, 0.2 seconds less the default value of 0.5 seconds—thereby reducing the dispense period as preselected by the user.

The liquid reservoir 16, as well as the other components of the ADM 11, including timer and controller 15 and power source 17, can be disposed on the outer surface of the outermost layer 12A of mask fabric, the inner surface of the innermost layer 12B of mask fabric, or in interstitial regions between layers 12A and 12B. The respiratory cycle detector 13 and droplet generator 14 of the ADM 11, however, will be located generally on the inner surface of innermost layer 12B of mask fabric and located close to the bottom of the nose (and near the mouth) to allow sensitive detection of the current phase and other parameters of the respiratory cycle (e.g., T1, T2, and T3). Locating respiratory cycle detector 13 and droplet generator 14 near the bottom of the nose also may allow the dispensed droplets to travel unimpeded through cavity 20 to the external openings to the nasal passages (i.e., the nostrils 19) of the user. Alternatively, droplet generator 14 may be placed on an interstitial surface or on the outer surface of the mask fabric provided that a suitable orifice is incorporated into innermost layer 12B and outermost layer 12A of fabric to allow free passage of the droplets from droplet generator 14 through cavity 20 to the nostrils 19 of the user. The respiratory cycle detector 13 may have a similar location provided that a suitable orifice is incorporated into outermost layer 12A and/or innermost layer 12B to allow exhaled air to reach respiratory cycle detector 13 unimpeded.

In some embodiments, the power source 17 for the ADM 11 is a rechargeable battery that is contained within an enclosure 17A (also referred to as a "housing"). A provision for connection to recharging cable 18 advantageously may be provided on the outer surface of the outermost layer 12A of the mask enclosure 12. Alternatively, the power source can be another portable power source, such as a non-rechargeable battery, a bank of capacitors that can be charged by solar cells, etc.

FIG. 1B shows that the shape of the face mask enclosure 12 can be adapted to wrap around the head and neck of the user to support comfortably the weight of the components of the ADM 11. For this purpose, the face mask enclosure 12 may include extension straps 12C that can be extended around the back of the head or neck of the user and secured to one another with an enclosure-fastener device 12D. Fastener device 12D may comprise the mating surfaces of a Velcro-type fastener, or fastener device 12D may comprise another type of complementary fastening mechanism such as mechanical clips, buttons, and the like. Alternatively, fastener device 12D may simply include fabric ties that can be tied together.

In some embodiments, respiratory cycle detector 13 comprises a primary sensor 13A and a reference sensor 13B. Generally, the primary sensor 13A will be located within the primary cavity 20 of the face mask system 10, close to the respiratory air flow where the primary sensor 13A is able to monitor a physical parameter affected by inspiration and exhalation of respiratory gases of the user. Respiratory cycle detector parameters are further discussed below. The reference sensor 13B will measure substantially the same parameter as the primary sensor 13A, but in contrast, will be located at another location that does not sense the flow of respiratory gases, preferably on the outside surface of the mask. For example, where the measured parameter is temperature, sensors 13A and 13B will be temperature sensors, and the primary sensor 13A will measure temperature of air inside the cavity 20 while the reference sensor 13B will measure temperature of ambient air external to the face mask system 10. Alternatively, where the measured parameter is either pressure or acceleration of a flexible membrane or flap, sensors 13A and 13B can be pressure sensors or accelerometers, respectively.

FIGS. 1A, 1B, and 1C include several different views of an embodiment of the automated liquid-droplet dispensing mechanism (ADM) 11 where the liquid reservoir 16 is attached directly to the droplet generator 14 without any intervening tubing or channels. With such a design, problems caused by blockage of the tubing or channels with air bubbles largely, if not entirely, can be avoided. Direct attachment of reservoir 16 to the droplet generator 14 also simplifies any cleaning or rinsing procedures that may be needed between an initial use and subsequent refilling of the liquid reservoir 16. Usually, the capacity of reservoir 16 will be determined by the amount of liquid that is needed for a specific interval of time. For example, the reservoir 16 may be designed to store the default dispensing volume needed for 10 hours in order to cover the vast majority of airline flights, work shifts, etc. The total volume of reservoir 16 usually will be between 10 milliliters (ml) and 100 ml, and preferably between 20 ml and 50 ml. In some embodiments, and as shown in FIG. 2, reservoir 16 has an opening 24, to allow the reservoir to be refilled, and a removeable cap 26, to seal the opening 24 to prevent leakage, so that the face mask system can be refilled with liquid conveniently, and thereby used multiple times.

One goal of the approach to automated liquid dispensing described herein is to minimize the amount of liquid required for adequate humidification of the upper respiratory tract of the user of the face mask system 10, and thereby allow the face mask system 10 to be compact, self-contained, and autonomous from peripheral supporting structures, such as support stands, liquid or vapor feed tubing, motors, compressors, power cords, and the like. Accordingly, the face mask system 10 is made to be practical and convenient to use where the mobility of the user is of paramount importance.

FIG. 2 shows a preferred embodiment where liquid reservoir 16 and droplet generator 14 are combined into a cartridge assembly 21 (also called a "cartridge") that includes opening 24 to allow the reservoir to be refilled and a removeable cap 26 to re-seal the opening 24 after refilling. Thereby, the cartridge assembly 21 can be refilled with liquid conveniently and used multiple times. The cartridge assembly 21 can further comprise a pad 22 that provides one or more electrical connections 23 to the timer and controller 15 discussed above with reference to FIGS. 1A, 1B, and 1C. Prior to first use of cartridge assembly 21 within a face mask system 10, the electrical connections 23 advantageously may be protected with a protective tape or film to cover the entire pad 22. The protective tape may be the "blue tape" that is commonly employed in commercial inkjet cartridges for the same purpose. Cartridge assembly 21 may be prefilled with a liquid reagent prior to first use. The same protective tape or film used to protect the electrical contacts 23 can also be applied to any exposed nozzles or dispensing apertures of droplet generator 14 within cartridge 21, thereby preventing leakage of liquid contained in reservoir 16 from the nozzles or dispensing apertures of droplet generator 14.

Overview of Reagents

Liquid reagents necessary to fill reservoir 16 of the subject invention may be supplied in kit form together with the self-contained, integrated face mask system 10. The liquid reagents of such a kit can be comprised of sterile or aseptic water. Optionally, the liquid reagents may include substances that provide for, and maintain, the normal composition of the ASLs of the respiratory tract. Such substances without limitation, generally comprise, in their normal physiological cationic forms, sodium ($Na^+$), potassium ($K^+$), calcium ($Ca^{++}$), magnesium ($Mg^{++}$), zinc ($Zn^{++}$), and the like. As counterions, usual substances, in their usual physiological anionic forms, include chloride ($Cl^-$), bicarbonate ($HCO_3^-$), phosphate ($H_2PO_4^-$, $HPO_4^{-2}$, and $PO_4^{-3}$), iodide ($I^-$), tri-iodide ($I_3^-$), and the like. Usual uncharged substances, especially those useful to maintain the potential of hydrogen ions (pH) and functionality of the airway surface liquids, include carbonic acid ($H_2CO_3$), hypoiodous acid (HOI), hydrochloric acid (HCl), phosphoric acid ($H_3PO_4$), ascorbic acid, and the like.

Because a substantial fraction of the dispensed aqueous liquid will evaporate after dispensation but before contact with the airway surface liquid (ASL) of the nasal cavities of a mask user, the concentrations of such substances provided to fill the reservoir 16 generally may be less than the concentrations normally found in the ASL of human nasal cavities. For example, where the mean evaporation of droplet volume is from 90 to 99 percent complete upon reaching the ASL, the concentrations of the substances to be provided in the liquid reagents may be supplied at 10 to 1 percent, respectively, of the concentrations normally found in nasal cavity ASL.

By way of further example, where sodium and chloride generally are present in the ASL at 50 to 150 millimolar (mM), and where the mean evaporation of droplet volume is 90 percent, these substances can be supplied as reagents in the reagent kit between 5 and 15 mM. On the other hand, where hypertonic electrolytes dispensed into the respiratory tract have been found to have beneficial effects, for example in the treatment of cystic fibrosis, then higher concentrations of electrolytes, for example from 50 to 150 mM (or even more), can be provided.

Another important substance in the ASL generally is the iodide anion. Iodide is concentrated from 10- to 50-fold above blood plasma levels by a sodium/iodide transporter protein bound to the cell membrane on the side of the airway epithelial cells facing the blood stream. The epithelial cells then release the concentrated iodide to the ASL via a nonspecific anion channel bound to the cell membrane on the opposite side of the cells (i.e., the side adjacent the ASL). Blood plasma iodide levels generally range from 0.5 to 2 micromolar (μM), and normal levels in the ASL generally range from 5 to 100 μM. Accounting for the 90 percent evaporation upon droplet dispensing, iodide therefore may be supplied in the reagent kit at between 0.05 and 10 μM. Normally, iodide in such reagent kits is supplied at between 0.5 and 1.0 μM, though iodide could be supplied in such reagent kits at higher or lower levels.

When respiratory epithelial cells are attacked by viruses or microbial organisms, these cells respond defensively by oxidizing the previously concentrated iodide in the ASL to hypoiodous acid (HOI) and elemental iodine ($I_2$). These oxidized iodine species appear not to attack the invading organisms directly, but instead appear to react biosynthetically to form specific iodinated compounds that interfere with the replication of viruses and bacteria. Therefore, under circumstances where there is a heightened concern, or increased risk of infection by a pathogen due to an ongoing epidemic, pandemic, crowded environmental conditions, or the like, users of the mask system 10 may want to utilize a reagent composition that provides for and maintains the ASL with a composition that is optimal for defense against such pathogens. In such cases, various oxidized iodine species may be provided in the reagent kit. The oxidized iodine species may be selected from several different forms, including hypoiodous acid (HOI), elemental iodine ($I_2$), or the tri-iodide anion ($I_3^-$) that comprises one molecule of elemental iodine and one molecule of iodide anion, or the like. All three of these oxidized iodine species are in chemical equilibrium, so it is relatively inconsequential which form is dispensed. It is important, however, that the oxidized species be stored in a stable form prior to dispensation by the droplet generator 14. The tri-iodide anion species may be the preferred species of oxidized iodine in some embodiments because it is highly stable and unreactive in storage, but upon dilution it dissociates into the more reactive elemental iodine ($I_2$) species, which in turn is in equilibrium with the even more reactive hypoiodous acid (HOI) species which appears to be the most effective at undergoing biosynthetic reactions that form substances that inhibit viral and bacterial replication. Customarily the tri-iodide anion will be supplied, for dispensing from a liquid reservoir 16, as the sodium or potassium salt at a final diluted concentration between 0.05 and 2.5 μM. More typically, the tri-iodide anion will be supplied at between 0.25 and 1.0 μM.

To store liquid reagents that are more stable in their concentrated form (using the tri-iodide anion as an example), the following approach may be used. The tri-iodide anion species can be supplied in a stable concentrated form, for example, as the well-known tincture of iodine that is an equimolar mixture of elemental iodine and the iodide anion. Generally, the composition of the tincture is about 2 percent iodine by weight and about 2.4 percent sodium iodide by weight dissolved in about 50 percent water and 50 percent ethanol. Alternatively, an equimolar ratio of iodine and iodide can be achieved by using about 2 percent iodine and about 2.6 percent potassium iodide (and similarly for other soluble iodide salts). As shown in FIG. 2, a small portion of the concentrated liquid tincture (or appropriate low dilution, for example, a 1/10 dilution) can be dispensed as a concentrated liquid aliquot into the inside of the cap 26, which may have a matrix of shallow holes 27 (e.g., that are between 0.1 and 0.5 millimeter (mm) in diameter and between 0.1 and 1.0 mm in depth) that function to retain the concentrated liquid aliquot by surface tension. A detachable sealing material 28 that is largely, if not entirely, impervious to water can then be used to seal the concentrated liquid aliquot of liquid reagent inside the cap 26. Alternatively, where chemical species within the liquid reagent are stable to drying, the droplets may be dried to a solid within the cap following dispensing of the liquid aliquot into the cap. In either case, the detachable sealing material 28 may be polyethylene, parafilm, cellophane, or the like. The removeable cap 26 can then be used to seal the opening 24 of the liquid reservoir 16 in a manner where the sealing material 28 continuously keeps either the liquid aliquot (or dried solid) containing the concentrated reagent from mixing with any larger volume of liquid that may be present in the reservoir 16. Prior to dispensing, the cap 26 can be removed (e.g., by the user) and the inner sealing material 28 covering the concentrated reagent can also be removed. The cap 26 then is replaced on the liquid reservoir 16 and the reservoir is shaken, allowing the bulk liquid in the reservoir to contact and mix with the concentrated reagent aliquot (or to dissolve the dried solid), which upon suitable mixing becomes diluted to the final desired concentration.

Overview of Controlled Droplet Dispensation

The volume of individual dispensed droplets customarily will be in the range of 1 attoliter ($10^{-18}$ liter) to 1 nanoliter ($10^{-9}$ liter). When spherical, the droplets generally will be from 0.1 to 100 micrometers (μm) in diameter. More typically, the droplets will be between 0.5 and 50 μm in diameter. Droplets dispensed by the droplet generator 14 of the face mask system 10 that are larger than 50 μm in diameter have a high probability of being deposited on the first surface that is encountered, such as on the surfaces of the nasal passages of the face mask user. Smaller droplets, in contrast, have an increased probability of reaching the lower respiratory tract of the face mask user, including the terminal alveoli of the lungs. It is generally accepted that droplets between 1 and 5 μm in diameter are most useful for delivery of dissolved substances to the alveolar tissues. Droplets even smaller will have the high probability of disappearing completely into the vapor phase (i.e., evaporating), and thus will be useful for the purposes of providing humidity but not for transporting dissolved solutes deep into the respiratory tract.

For purposes of delivering only water vapor (humidity) to the respiratory tract, the broadest range of droplet sizes from droplets that are about 0.1 μm in diameter (about 0.5 attoliter in volume) to about 100 μm in diameter (about 0.5 nanoliter in volume) may be used. Several types of droplet generators can dispense droplets in this size range, including vibrating mesh nebulizer (VMN) dispensers, piezoelectric inkjet (PIJ) dispensers, and thermal inkjet (TIJ) dispensers. Inkjet dispensers generally are used to dispense droplets from nozzles for printing applications, usually in the 1-100 picoliter range, and generally are driven at frequencies of 1-50 kilohertz (kHz) for repeated dispensation from each nozzle. In contrast, VMN dispensers can operate at higher frequencies (e.g., 100 kHz or more), thereby providing for the desired liquid dispensing rates (as measured in liquid volume dispensed per unit time) while still making it possible to deliver much smaller droplets. Droplets as small as 0.1 μm in diameter (0.5 attoliter in volume) may be formed and dispensed by a VMN dispenser by making correspondingly small holes in the plate (also referred to as the "disc") through which liquid is directed. Larger holes in the plate will allow for the formation of larger droplets that can then be dispensed. The VMN dispensers are highly versatile and provide for dispensing a wide range of droplet sizes over a wide range of liquid volumetric dispense rates. The VMN dispensers also operate with relatively low power and are light in weight and therefore are generally preferred as the droplet generator 14.

Figures 3A, 3B:
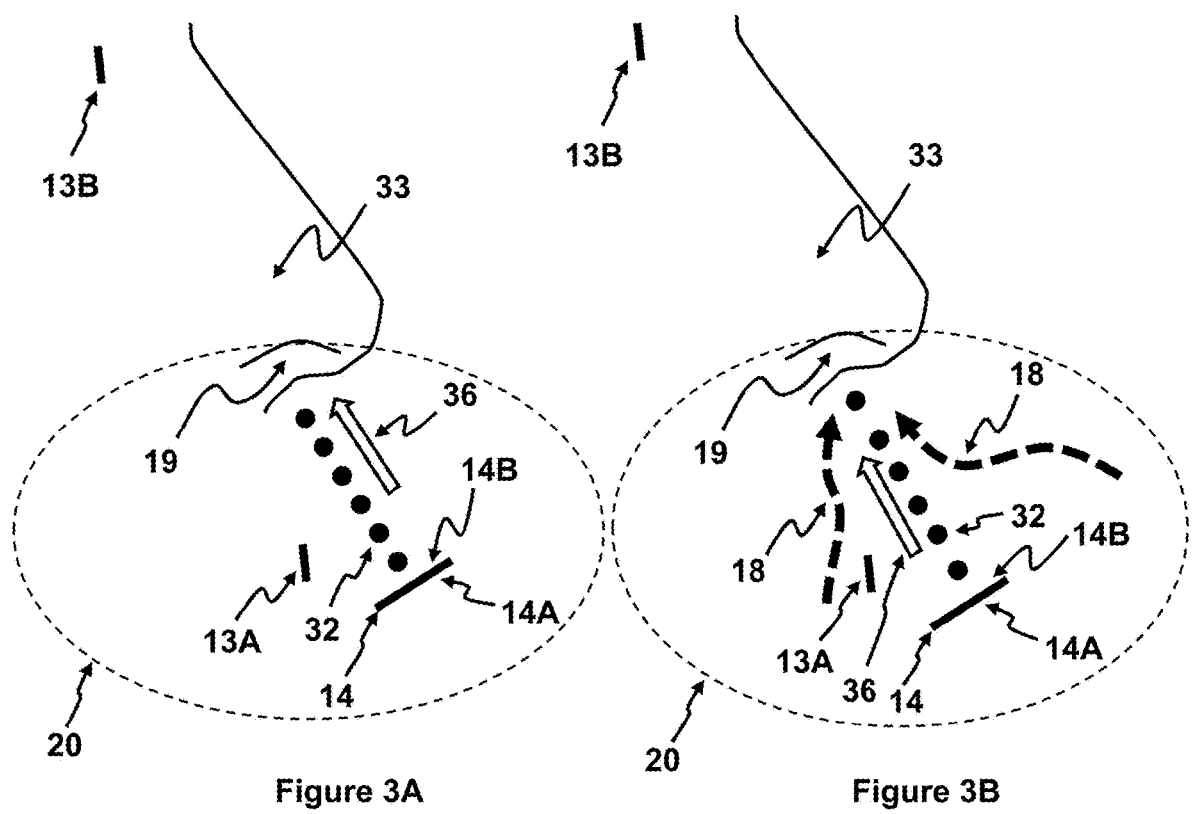
FIG. 3A shows a preferred placement of the droplet generator of the ADM within the primary cavity, wherein the droplets are dispensed laterally and vertically, generally on axis with the outermost nasal passages of the user.
FIG. 3B illustrates how inhaled air flow may facilitate the flow of droplets along a preferred path toward the nasal passages of the user within the primary cavity that is formed between the face mask enclosure and the face of the user.

FIG. 3A shows a preferred embodiment where the plate of a VMN dispenser is placed within the primary cavity 20 of a face mask system and employed as a droplet generator 14. As mentioned above, the droplet generator 14 is usually attached to an interior surface of the face mask, so as to be located within a primary cavity 20 formed between the inner layer of the face mask fabric and the nostril openings 19 into the nasal passages of the user. The dimensions of the primary cavity 20 will depend on the anatomy of individual users, as well as on the breathable fabric(s) used for the outermost and innermost layers of the face mask system. Generally, the primary cavity 20 will measure between about 0.5 and 3 centimeters (cm) from the innermost layer of face mask fabric to the external nostril openings 19 of the nasal passages.

In FIG. 3A, a droplet generator 14, that may be a VMN-type droplet generator, having a plate that is positioned such that a pulse of liquid droplets 32, arising from liquid supplied on the first side 14A of the plate having ingress holes is emitted from a second side of the plate 14B having egress holes of the droplet generator 14, so as to travel generally laterally and vertically, generally parallel to a set of axes (shown by arrow 36) that pass into the nostrils 19 and then into the nasal passages 33 of the user. This second side of the plate 14B may be referred to as the "droplet-emitting surface." Advantageously, this placement of the droplet generator 14 can minimize the loss of droplets prior to entry into the nasal passages. FIG. 3B shows the same embodiment as FIG. 3A, but additionally shows the effects of air flow into the nostrils 19 during inhalation of air by the user of the face mask. Airflow stream 18, during inhalation, acts as a guiding force on any droplets that may stray from the desired path and direct them back onto a preferred path along a set of axes (shown by arrow 36) that are directed into the nostrils 19 of the nose.

The kinetic energy of the dispensed droplets 32, as well as the force of gravity, will affect the path of the dispensed droplets 32. In embodiments where PIJ dispensers or TIJ dispensers are used to dispense the droplets, the initial velocity v of the dispensed droplets generally will be between 5 and 20 meters per second (m/sec). Droplets with mass m and mean velocity v will have kinetic energy of ½ $mv^2$ and will be able to travel upward against the acceleration of gravity g tor a maximum distance of h, where ½ $mv^2$=mgh. Solving for the maximum distance h shows that the droplets may be able to travel upwards as high as 5 meters or more. Air resistance, however, creates drag that generally limits the distance of upward travel to less than 5 meters. The effect of drag from air resistance is insignificant compared to the kinetic energy of dispensed droplets having volumes at least in the picoliter range, especially for short (e.g., 0.5-3.0 cm) distances from the droplet generator 14 to the nostrils 19 of the nose of the user. Therefore, the kinetic energy of larger dispensed droplets (e.g., those exceeding one picoliter in volume) will be important to their direction of travel. Consequently, PIJ and TIJ dispensers must be carefully positioned and aimed. Conversely, for smaller droplets in the femtoliter and sub-femtoliter ranges that are dispensed by VMN dispensers, the effect of air resistance (drag) is much greater. With these smaller dispensed droplets, the effects of the airflow stream 18, during inhalation, as shown in FIG. 3B are much greater and play a beneficial role of guiding the dispensed droplets into the nostrils 19 of the user. Advantageously, the smaller droplets that can be dispensed by VMN dispensers are normally in the range of 0.1 to 100 femtoliters in volume.

Overview of Respiratory Cycle Detector

FIGS. 3A and 3B show an embodiment of the face mask system where sensor 13A included as a component of the respiratory cycle detector is a temperature sensor. These drawings show only the portion of the face mask system needed to explain more clearly operation of the respiratory cycle detector. In this temperature-sensing embodiment, under conditions of exhalation, sensor 13A will indicate roughly the body temperature of the user (e.g., 37° C.). When the inhalation phase of the respiratory cycle begins, the inhaled air flow that is shown by arrows 18 in FIG. 3B will encounter sensor 13A, thereby altering its temperature to approach that of the inhaled air, which is normally cooler than the body temperature of the user. Accordingly, temperature measurements generated by sensor 13A may be used (e.g., by timer and controller 15) to determine whether the user presently is inhaling or exhaling.

In another embodiment, sensor 13A is paired with a reference sensor 13B. For example, if sensor 13A is a temperature sensor as discussed above, then sensor 13B may be a reference temperature sensor that is situated outside of the mask and positioned to monitor the environmental temperature (also referred to as the "ambient temperature"). Reference sensor 13B can send a reference signal to the timer and controller 15 that can be compared to the signal produced by temperature sensor 13A that is disposed within the primary cavity 20 within the mask. The reference signal may be representative of a stream of sequential temperature measurements generated by reference sensor 13B, and advantageously averaged over several seconds or minutes (e.g., to minimize noise). The signal generated by sensor 13A situated within primary cavity 20 of the face mask enclosure 12 may also be representative of a stream of sequential temperature measurements in order to minimize noise, but in contrast, must be averaged over a much shorter time period (e.g., from 1 to 200 milliseconds for respiratory cycles of usual periods from roughly 0.5 to 3 seconds in duration). Advantageously, the reference sensor 13B may be used to reduce environmental variations to further improve the accuracy of the determination made by the timer and controller 15 that triggers the beginning and end of droplet dispensing by droplet generator 14. In embodiments where the respiratory cycle detector 13 relies on analysis of temperature measurements (e.g., temperature measurements generated by sensor 13A and reference sensor 13B) to determine when dispensation should be triggered by the timer and controller, the triggering can be predetermined to occur by a ratio of the signals sent by sensor 13A and 13B to the timer and controller. For example, triggering can be predetermined to occur upon a fractional approach (e.g. a ratio in the range of 2 to 10 percent) from the highest exhalation temperature measured by sensor 13A to the environmental temperature measured by reference sensor 13B. For example, if (i) sensor 13B measures the environmental temperature to be 23° C., (ii) the maximum exhalation temperature measured by sensor 13A within the primary cavity 20 of the mask is 37° C. (i.e., producing a difference of 14° C.), and (iii) the predetermined fractional approach is set to be 7.14 percent, then droplet dispensing would be triggered by the timer and controller when the temperature measured by sensor 13A changes from 37° C. to 36° C. (i.e., 1/14th or 7.14% of the temperature difference). For usual respiratory cycles of humans (e.g., occurring at about 0.5 Hz), the greatest signal-to-noise ratio will be achieved when sensor 13A has a response time faster than 0.2 seconds (e.g., between 50 and 200 milliseconds). When this is the case, the fractional change needed for triggering of droplet dispensing by the timer and controller may be at the higher end of the range (e.g., near 10 percent). Alternatively, when the response time of sensor 13A is relatively slow (e.g., greater than 1 second), then the fractional change needed for triggering of droplet dispensing may be at the lower end of the range (e.g., near 2 percent). Hence, a faster time response of sensor 13B can improve the signal-to-noise ratio, as received by the timer and controller 15, which results in improved precision, with less hysteresis (i.e., less response delay), for triggering of dispensing by droplet generator 14. Electronic noise reduction techniques may be applied by timer and controller (as discussed above) to further increase the signal-to-noise ratio. For example, the incoming signals from the respiratory cycle detector can be averaged over 1 to 100 milliseconds, thereby reducing noise in the data. As another example, a Savitzky-Golay filter may be applied to the incoming signals over 1 to 100 millisecond intervals. The duration of the droplet dispensing sequence triggered by the timer and controller (i.e., the dispense period) usually will be for a duration between 0.05 and 0.8 seconds (and more typically between 0.1 and 0.5 seconds). To allow for longer or shorter dispense periods, the timer and controller adjuster adjustment device 15A may be attached to an exterior surface of the outermost layer 12A of the mask enclosure (as shown in FIGS. 1A, 1B, and 1C) to allow the user to increase or decrease the duration of the dispense periods (as discussed above).

Several alternative means are available for detecting the inhalation and exhalation phases of the respiratory cycle. For example, sensor 13A could be a differential pressure sensor that compares the pressure within the primary cavity 20 inside of the mask enclosure to the pressure outside of the mask enclosure (thereby performing the functions of both sensors 13A and 13B). For such differential pressure comparisons, a similar algorithm to that described above for temperature changes by sensors 13A and 13B could be used by the timer and controller 15 to trigger the beginning of a sequence of droplet dispensing by droplet generator 14. Other alternative sensors whose outputs could be used to determine the instant phase of the respiratory cycle of the user of the mask system include nasal capnometers, nasal pressure transducers, accelerometers including abdominal accelerometers, transpulmonary electrical impedance monitors, peritracheal microphones, sensors for photoplethysmography, and the like.

Figure 3C:
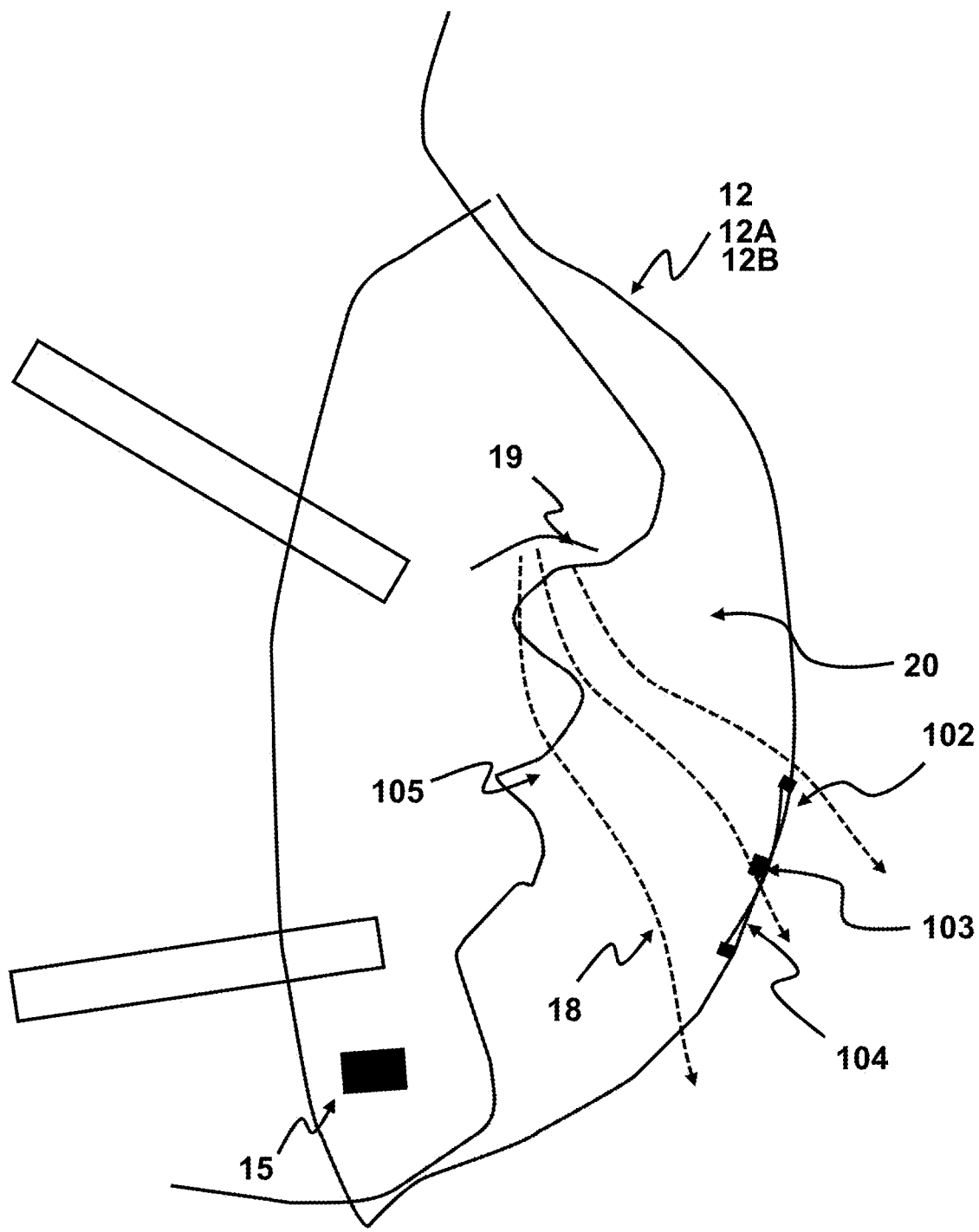
FIG. 3C shows a portion of an embodiment of the face mask system where the respiratory cycle detector of the ADM comprises an accelerometer that is placed on a thin, flexible, region of the face mask enclosure.

FIG. 3C shows an embodiment where an accelerometer 103 is placed (e.g., fixedly mounted) on a thin, flexible membrane 104 that is situated in a sensing region 102 of the mask enclosure 12. In some embodiments, the accelerometer 103 can be part of an inertial measurement unit (IMU) that includes a combination of accelerometer(s), gyroscope(s), and/or magnetometer(s) that monitor motion of the face mask system. For increased sensitivity the flexible membrane 104 may be substituted into an opening in the mask enclosure 12, for fabric layers including layers 12A and 12B. Alternatively, the accelerometer 103 simply may be secured to the innermost layer 12B of mask fabric (and in this way monitor the movement of innermost layer 12B due to air movement within the primary cavity 20). Regardless of its position with respect to the outermost layers layer 12A and innermost layer 12B of mask fabric, the accelerometer 103 is responsive to the inhalation and exhalation phases of the user's respiratory cycles by monitoring the air movement within the primary cavity 20. In response to the air movement, accelerometer 103 sends a signals to the timer and controller 15 for processing that, when processed, trigger dispensing of droplets into the primary cavity 20. Said another way, measurements generated by the accelerometer 103 can be examined to identify reversals of direction of the air flow 18 that occur when the respiratory cycle changes from the exhalation phase to the inhalation phase. The sensitivity of detection of the user's respiratory cycles can be increased by placing the sensing region 102 of the mask enclosure 12 near the nostrils 19 and mouth 105 of the mask user, where the airflow 18 during inhalation and exhalation is the greatest.

Power consumption by sensors such as accelerometers and temperature sensors (e.g., thermocouples or thermistors) can be very low. Low consumption of power allows power source 17, as shown in FIGS. 1A, 1B, 1C, and 8A, to be small and lightweight. Typically, current draw during operation of the face mask system 10 is between 1 to 100 ptA, and in a standby mode may be as low as 0.1 µA. For 10 hours of operation, the energy consumption (as determined by multiplying power consumption and duration) may be between 0.1 and 1.5 joules. Several suitable microelectromechanical system (MEMS)-based accelerometers are available commercially and well-suited for the face mask system 10 of the present disclosure. These accelerometers include the LIS2DS12, MIS2DH, and IIS2ICLX devices manufactured by ST Microelectronics. The LIS2DS12 device is a 3-axis accelerometer with a form factor of 2 mm×2 mm×0.86 mm. In its most sensitive range (±2 g range), sensitivity is 0.061 mg/digit. The MIS2DH device is also a 3-axis accelerometer with a form factor of 2 mm×2 mm×1 mm. In its most sensitive range (±2 g range), sensitivity is 0.98 mg/digit. The IIS2ICLX device is a 2-axis accelerometer with a form factor of 5 mm×5 mm×1 mm. In its most sensitive range (±0.5 g range), sensitivity is 0.015 mg/digit.

Figure 3D:
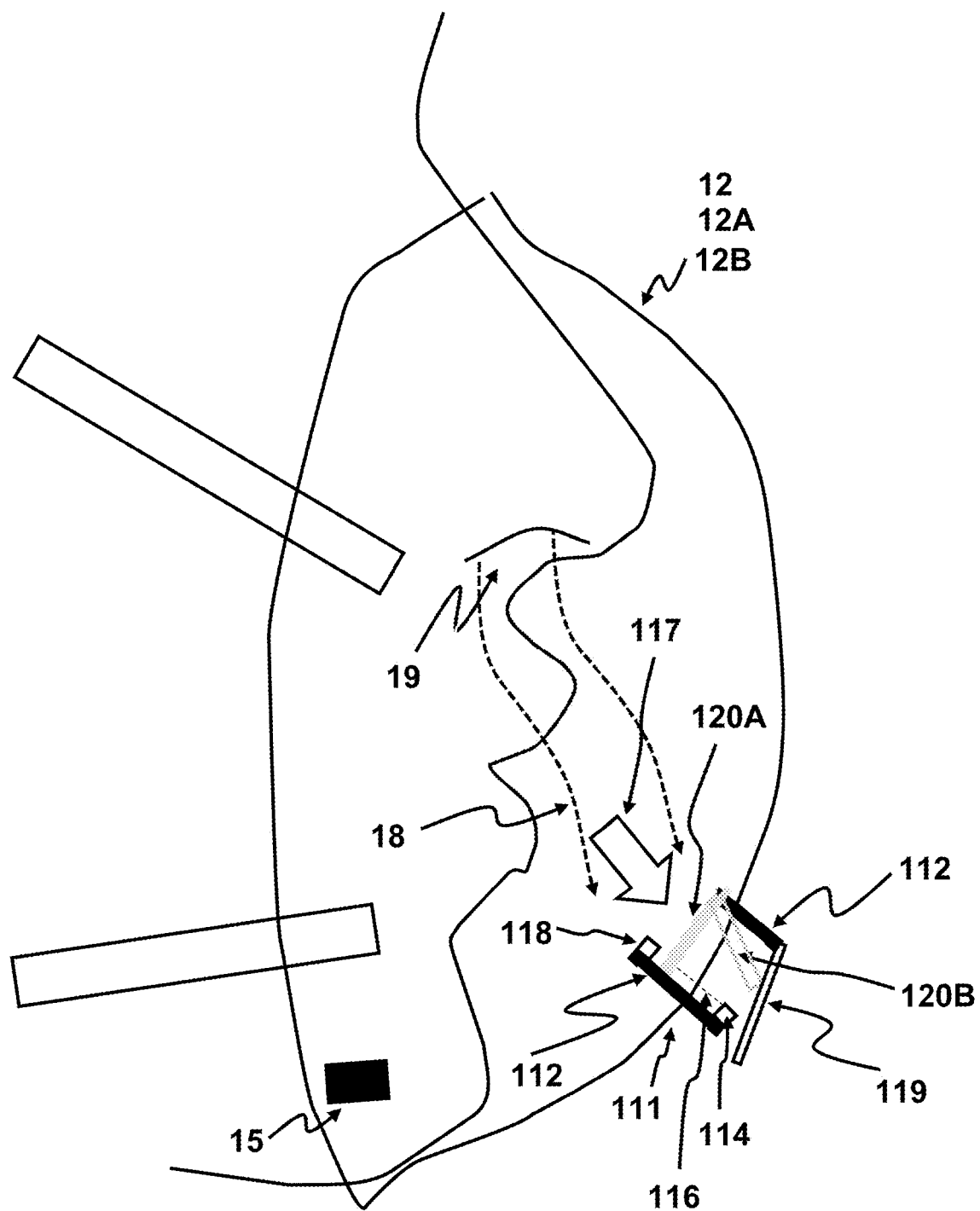
FIG. 3D shows a portion of another embodiment of the face mask system where the respiratory cycle detector of the ADM comprises a photo-interrupter that is placed in an exhalation valve that is fixedly attached to the face mask enclosure.

In some respiratory cycle detector embodiments, an accelerometer 103 can be attached to a movable flap (120A and 120B) instead of to the flexible membrane 104 that is shown in FIG. 3C. FIG. 3D shows such a movable flap both in a closed position 120A and in an open position 120B. The movable flap may reside in an exhaust valve 112 that alternately closes during inhalation and opens during exhalation. Movement of the flap between the closed position 120A and open position 120B alternatively could be monitored by a photo-interrupter mechanism, as shown in FIG. 3D. In such photo-interrupter embodiments, a light source 114 can direct a light beam 116 on a path toward a photodetector 118. The light source 114 may reside on one side of the movable flap while the photodetector 118 may reside on the other side of the flap. When the moveable flap is substantially opaque, the light beam 116 may not be detectable by the photodetector 118 when the flap is in the closed position 120A, but can be detected when the flap is in the open position 120B. The movable flap can be situated within exhaust value 112 so that the movable flap normally resides in the closed position 120A over the course of a respiratory cycle of a mask user except during the exhalation phase. Therefore, during the inhalation phase of the user's respiratory cycle, light beam 116 is blocked by the movable flap which is in the closed position 120A, and light fails to reach photodetector 118. Upon exhalation by the user, the flap moves to its open position 120B and the photodetector 118 thereupon receives the light beam 116 and creates an electrical signal that can be transmitted from the photodetector 118 to the timer and controller 15 for processing.

The electrical signal can be processed to "pre-arm" the timing and controller 15. Following the pre-arming, the timer and controller can send a signal to the droplet dispenser to begin droplet dispensing upon return of the movable flap to its normally closed position 120A, whereupon the light beam 116 again is blocked from reaching photodetector 118 and the electrical signal from the photodetector 118 that is sent to the timer and controller 15 is terminated. Termination of the electrical signal sent to the timer and controller, following the pre-arming event, may then prompt the timer and controller 15 to trigger the droplet dispenser to dispense a sequence of droplets for the dispense period, the length of which may be for either a predetermined period or a period determined by a computed algorithm (as discussed previously).

To further improve the signal-to-noise ratio of the photo-interrupter mechanism, the light source 114 can be modulated at a predetermined frequency (e.g., 10 kHz). The light source 114 may be, for example, a light-emitting diode (LED) or another illuminant. In this case, the photodetector 118 may have an electronic bandpass filter that provides an output signal that is substantially proportional to the modulated light only (and independent of continuous light that creates a direct current or light that is modulated at other frequencies). Exhaled air that passes through the exhaust valve 112 and actuates the movable flap optionally may be filtered by a porous fabric filter material 119. Additionally or alternatively, the exhaled air may be directed downward into the clothing of the user by a material 119 that facilitates the removal of respiratory droplets from the exhaled air prior to being expelled into the ambient environment.

The timer and controller 15, as shown in FIGS. 1A, 1B, 1C, 3A, 3B, 3C, and 3D, can be configured to generate a dispense "start" signal at T1, in response to determining in real time based on analysis of the measurements generated by respiratory cycle detector 13, that an exhalation phase has ended, and an inhalation phase has begun. The timer and controller 15 can receive information from respiratory cycle detector 13 that comprises, for example, sensor 13A and/or reference sensor 13B and then the timer and controller 15 can process the information to determine the precise instant in time to send the "start" signal to the droplet generator 14 to begin dispensing. The timer and controller 15 also can control the interval of time following the turn-on-time that the dispensing continues uninterrupted. This interval of time may be referred to as the "dispense period. Dispensing may be configured as a pulse of multiple droplets that are dispensed simultaneously during a dispense period, or dispensing may be configured as a sequence of individual droplets that are dispensed sequentially during the dispense period. The timer and controller 15 may be representative of a group of discrete electronic components, such as comparators, transistors, one-shot multivibrators (also referred to as "monoflops"), or bistable multivibrators (also referred to as "flipflops"). For example, a comparator can be used to compare the voltage output by respiratory cycle detector 13 to a predetermined voltage threshold, above which the comparator output is considered "high." A monoflop can be used to modify the voltage output of the comparator to a desired pulse width. Then, the output produced by the monoflop can be fed into the base of a transistor switch that ultimately controls the driver of droplet generator 14. Accordingly, the dispense period can be determined electronically and applied for a predetermined amount of time, though this predetermined amount of time could be varied as discussed above. The dispense period may triggered by a "start" signal that is sent by timer and controller 15 to droplet generator 14 immediately following the condition of a "high" comparator output. Alternatively, the dispense period may be triggered by a "start" signal that is sent by timer and controller 15 to droplet generator 14 after a delay period whose length is predetermined or calculated as discussed above.

In some embodiments, the timer and controller 15 comprises a solid-state microprocessor that includes memory to enable storage of firmware- or software-implemented instructions. The microprocessor may be able to emulate the functions of comparators, transistors, monoflops, and flipflops. Microprocessors can further process the input signal from the respiratory cycle detector 13 to reduce noise. Because predetermined parameters can be stored in the memory of a such a microprocessor and changed when desired, such a microprocessor can facilitate changing operational parameters, from time to time, to improve operation of the droplet generator 14 within the mask system 10.

A microprocessor also may be able to facilitate the operation of certain types of alternative droplet generators, including TIJ or PIJ dispensers. A combination of a clock, a counter, and a demultiplexer can be used to send pulses in sequence to the driver of a TIJ dispenser or a PIJ dispenser. The counter may be responsible for counting clock cycles and then storing information on how many clock cycles have passed. This information then can be used by the microprocessor to send the "start" and "end" signals, as determined by the timer and controller, to a demultiplexer that, based on information in the "start" signal, addresses a selected output (e.g., to begin the dispense period at a selected nozzle of a TIJ or PIJ dispenser). Other aspects for controlling and driving TIJ and PIJ dispensers, as adapted for use in the instant face mask technology, are described below.

Overview of Droplet Generators

As discussed above, the droplet generator 14 may be responsible for commencing and then concluding dispensation of liquid droplets from a reservoir 16 based on signals received from the timer and controller 15. Generally, dispensation begins when the inhalation phase commences, so as to humidity air that is drawn into the nostrils or mouth of the user during the inhalation phase. However, dispensation may end before the inhalation phase concludes, such that dispensation occurs over only an initial portion of the inhalation phase. Such an approach can help to ensure that a cavity defined by the innermost layer 12B of the face mask fabric and the face of a mask user does not become "over-humidified," which could result in liquid water saturating the layers 12A and 12B of breathable fabric of the face mask system 10, rendering it inoperable.

The droplet generator 14 can take several different forms depending on the goals and constraints of the face mask system 10. These different forms are further discussed below. Regardless of its form, the droplet generator 14 generally is configured to direct a sequence of droplets 32 towards the nostril openings 19 of the nasal passages 33 of the mask user. Liquid can be dispensed through holes in a plate by applying pressure by vibration, for example, by a VMN dispenser. Alternatively, liquid can be dispensed through nozzles by inducing a volume change, for example, by a PIJ dispenser or a state change (e.g., from liquid to gas), for example, by a TIJ dispenser.

Figure 4A:
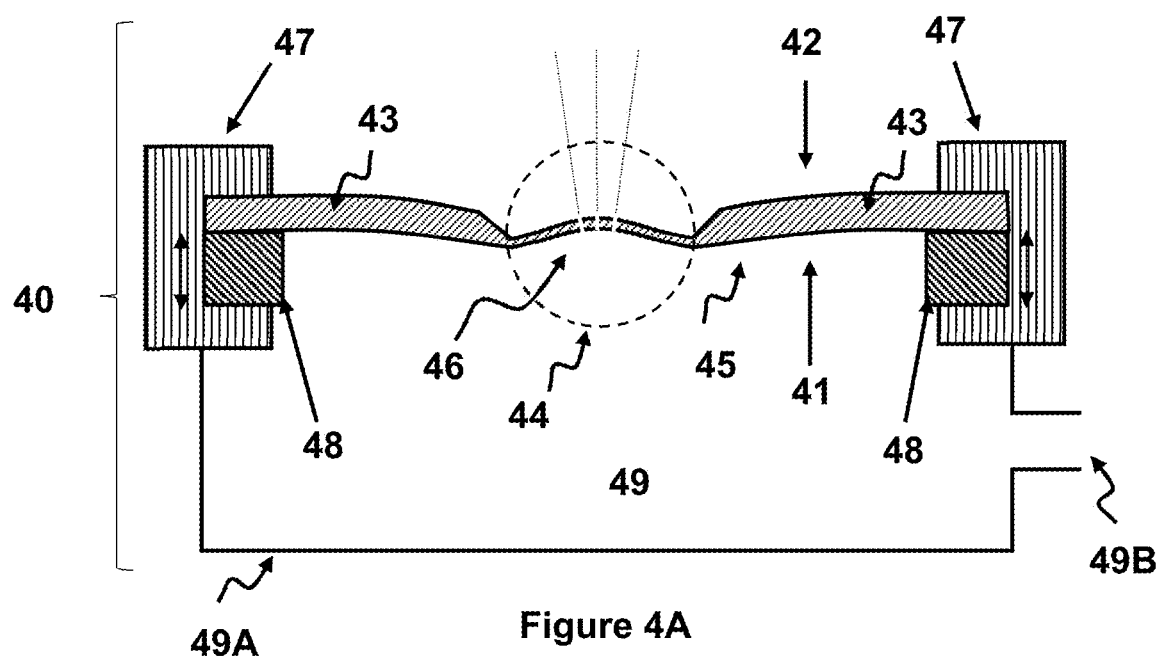
FIG. 4A shows an embodiment of the face mask system where the droplet generator of the ADM is a vibrating mesh nebulizer (VMN) dispenser that includes a plate (also referred as a "disc") for directing droplets upward.
Figure 4B:
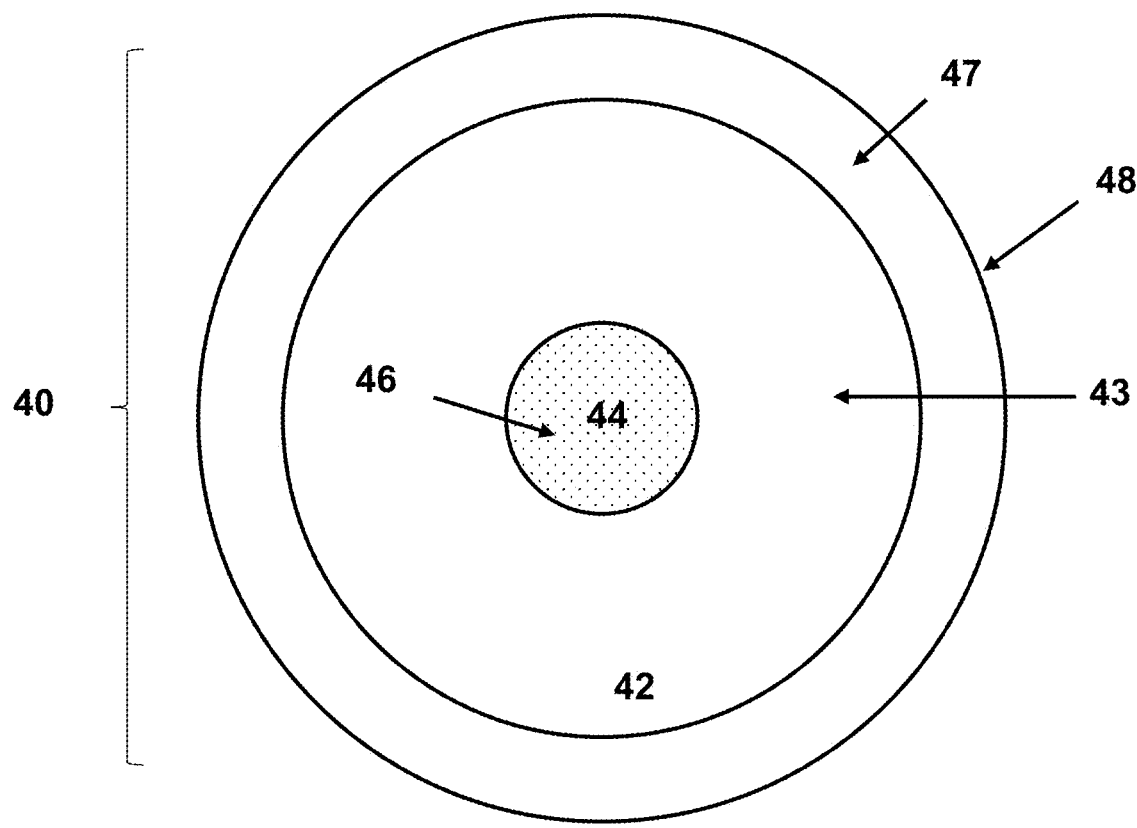
FIG. 4B shows a top view of the plate shown in FIG. 4A.
Figure 5:
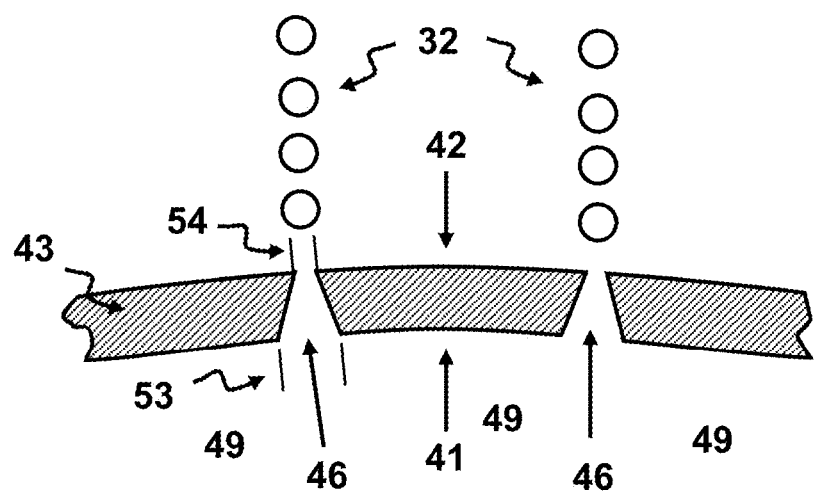
FIG. 5 shows liquid droplet formation and droplet dispensation from tapered apertures of the plate of a VMN dispenser.

As an example, in embodiments where small droplets (e.g., not exceeding one nanoliter in volume) are desired, the droplet generator 14 may comprise a VMN dispenser 40 that includes a plate 43, as shown in FIGS. 4A, 4B, and 5. A side view of the VMN dispenser 40 and plate 43 is shown in FIG. 4A, and a top view of the VMN dispenser 40 and plate 43 is shown in FIG. 4B. The plate 43 can have channels defined therethrough that, when vibrated, emit droplets of liquid. The plate 43 may have one or more ingress holes along a first side 41 (also referred to as the "liquid-accepting side") through which liquid is able to enter the plate 43. Each ingress hole is connected through at least a portion of the plate to one or more corresponding egress holes on a second side 42 (also referred to as the "liquid-dispensing side") through which liquid is able to exit the plate 43. When the plate 43 is ultrasonically vibrated by a vibration element, liquid is induced to flow into the plate 43 from the liquid-accepting side 41 and then ejected in the form of droplets from the liquid-dispensing side 42.

As shown in FIGS. 4A and 4B, the plate 43 may be a thin metal disc with a central portion 44 that contains a plurality of tapered apertures 46 that are arranged in an array. The term "mesh nebulizer" comes from this array of apertures 46 as shown in FIG. 4B, which look like a mesh. Advantageous for dispensing, as shown in FIG. 5, the apertures 46 may have their largest diameter 53 on the liquid-accepting side 41 of the plate 43 that is in contact with a liquid 49 to be dispensed. The apertures 46 may taper to a smaller diameter 54 on the liquid-dispensing side 42 of the plate 43. The larger diameter 53 on the liquid-accepting side 41 of the plate 43 generally will be between 20 and 50 μm. The smaller diameter 54 on the liquid-dispensing side 42 of the plate 43 generally will be between 0.5 and 8 μm (and more typically between 0.5 and 2 μm).

The diameter of the generated droplets is approximately the same as the diameter of the holes on the liquid-dispensing side 42 of the plate 43. Suitably small, tapered holes, with their smallest diameter between 0.5 to 2 μm, can be employed to predetermine the size of the droplets. Vibration of the plate 43 can be initiated by a vibration element, such as a ring-shaped piezoelectric transducer 48 that is located around the perimeter of the plate 43 as shown in FIGS. 4A and 4B. The vibrational frequency usually will be in the ultrasonic frequency range between 50 and 500 kHz (and more typically between 100 and 120 kHz) and at the resonance frequency of the plate 43. The vibration causes a time-varying pressure wave that forms droplets of liquid at the liquid-dispensing side 42 of plate 43. A flexible gasket 47 may act to keep plate 43 in contact with the piezoelectric transducer 48, as well as to seal the plate 43 to a liquid-retaining chamber 49A that contains the liquid 49 to be dispensed and provides for a route of liquid re-supply 49B from the main body of liquid reservoir 16. Initiation of vibration at the perimeter of the plate 43 by the piezoelectric transducer 48 can consequently cause the central portion 44 of plate 43 to vibrate at the frequency of piezoelectric transducer 48, but at an increased amplitude. The amplitude of the vibration in the central portion 44 of plate 43 affects the rate of liquid droplet dispensing. Droplet dispensing is most energy efficient if the vibrational frequency coincides with a resonant mode of the plate 43. The vibrational amplitude of the central portion 44 of plate 43 can be increased further by thinning the disc material in the central portion 44 of plate 43 or by increasing the power applied to the piezoelectric transducer 48. The liquid 49 that is to be dispensed as liquid droplets commonly is said to be "atomized" by the VMN dispenser 40 (also referred to as the "VMN assembly").

FIG. 5 shows in greater detail the tapered shape of apertures 46 in the plate 43. The metal in the central portion 44 of plate 43 is generally between 50 and 250 □m in thickness, and plate 43 may be comprised of stainless-steel or a similar durable, corrosion-resistant material. Usually, the plate 43 is comprised of a metallic material. When the central portion 44 of the plate 43 is in the shape of a dome (e.g., hemispherical, arc-shape, parabolic, or curved), the vibrational amplitude is more uniform throughout the central portion 44 of the plate 43. Accordingly, droplets 32 dispensed from the apertures 46 are more uniform size. For this reason, the central portion 44 of plate 43 generally will be dome-shaped (and thus concave to the liquid-dispensing side 42 of the plate 43). Commercially available plates for VMN dispensers are normally about 16 mm in diameter and have a piezoelectric transducer 48 that is annular in shape and about 4 mm in width. The central portion 44 of the plate 43 is about 4 mm in diameter. For such a structure, the resonance vibrational frequency is about 110 kHz. A functioning VMN dispenser can be connected to a liquid-retaining chamber 49A that is filled with an aqueous solution 49. To ensure that liquid does not escape from the liquid-retaining chamber 49A, a sealing gasket 47 may be situated along the perimeter of plate 43. The sealing gasket 47 may be made of rubber or another elastic material, and may be about 20 mm in diameter. The piezoelectric transducer 48 that serves as the vibrating actuator for the plate 43 may be driven by a piezoelectric crystal oscillator that vibrates at a resonant frequency of about 110 kHz. The voltage needed to drive the piezoelectric transducer 48 is normally between 16 and 50 volts. Meanwhile, the driver circuit that is responsible for controlling the VMN dispenser can comprise an oscillator, a metal-oxide-semiconductor field-effect transistor (MOSFET) driver, and a DC-to-DC power converter that steps up voltage from its input level to its output level. In operation, a low-voltage signal (e.g., at 110 kHz) from the oscillator can be fed into the gate of the MOSFET driver that modulates the higher voltage supplied by the DC-to-DC power converter, and thereby supplies the higher voltage signal (e.g., at 110 kHz) that drives the plate 43 of the VMN dispenser 40.

In a preferred embodiment, the VMN dispenser comprises a plate 43 that is 16 mm in diameter with an annular or ring-shaped piezoelectric transducer 48 located along its perimeter that is roughly 4 mm wide. The piezoelectric transducer 48 can be electrically driven by the oscillator as discussed above. A precision timing circuit, such as a NE555 timing device manufactured by Texas Instruments, together with a tuning resistor circuit, can be used to tune the oscillator to the desired resonant frequency. The NE555 timing device may also have associated trigger circuitry that can be used for synchronizing the output of the VMN dispenser to the respiratory cycle of the user. A conventional power converter, such as the MC34063a DC-to-DC power converter manufactured by Texas Instruments, may be suitable for boosting the lower voltage signal (e.g., at 16 volts) to the higher voltage signal (e.g., at 50 volts) needed to drive the piezoelectric crystal. The plate 43 may consume 1-1.5 watts (W) of power when it is generating aqueous liquid droplets at a rate of approximately 22 mg/sec. Therefore, to dispense a full reservoir of 36 grams of aqueous liquid, the energy required is about (1-1.5 W)☐36 g/(22 mg/sec)=1.6-2.5 kJ.

A power source 17 that is able to provide at least 1-1.5 W of power can be designed and/or selected for the face mask system 10. Options include rechargeable lithium-ion (Li-ion) batteries and lithium-polymer (Li-polymer) batteries with an output voltage between 3.0 and 3.7 V. At this voltage, the required 1.6-2.5 kJ of energy can be supplied by 127-190 milli-ampere hour (mAh) of current capacity. Li-polymer batteries that meet the power and energy requirement include the DTP502535 battery manufactured by Data-Power Technology that has an energy capacity of 400 mAh and a peak discharge current of 400 milliampere (mA) (1.36 W). Similarly, the LIPO552530 battery manufactured by PK Cell has an energy capacity of 350 mAh and a peak discharge current of 350 mA (1.3 W).

The droplet generator 14 preferably dispenses about 5 milligram (mg), with an adjustable range from 1 to 20 mg, of liquid water droplets during each respiratory cycle of a user of the face mask system. Therefore, with a dispense rate of 22 mg/sec, the VMN dispenser will require a droplet-dispensing sequence, or dispense period, that is about 0.23 seconds in duration. If an individual user desires a lessor, or a greater, quantity of dispensed liquid droplets during each respiratory cycle, the timer and controller adjustment device 15A will decrease, or increase, the dispense period of the liquid droplet dispensing sequence during each respiratory cycle. The maximum duration of the dispense period during a particular respiratory cycle will be approximately the total length of the inhalation portion of that respiratory cycle, roughly 1 second.

In addition to the placement of one or more control mechanisms (e.g., timer and controller adjustment device 15A) on the outermost layer 12A of the face mask system, the user may be able to control the rate of droplet dispensing remotely and wirelessly, for example, through a computer program (e.g., a mobile application) executing on a computing device (e.g., a mobile "smart" phone). Operation times, dispense power, and dispense sequence durations may be remotely selected through the computer program. Remote control communication between the face mask system 10 and the computing device may be performed through standard wireless communication protocols, such as Bluetooth, ZigBee, WiFi, and the like provided that the appropriate receivers are incorporated into the face mask system 10. A Near Field Communication (NFC) protocol could be used provided that the computing device is moved to within a few centimeters of an NFC receiver appropriately placed within the face mask system 10 (e.g., on the outer surface of the outermost layer 12A of the face mask enclosure near the timer and controller 15).

Figure 6:
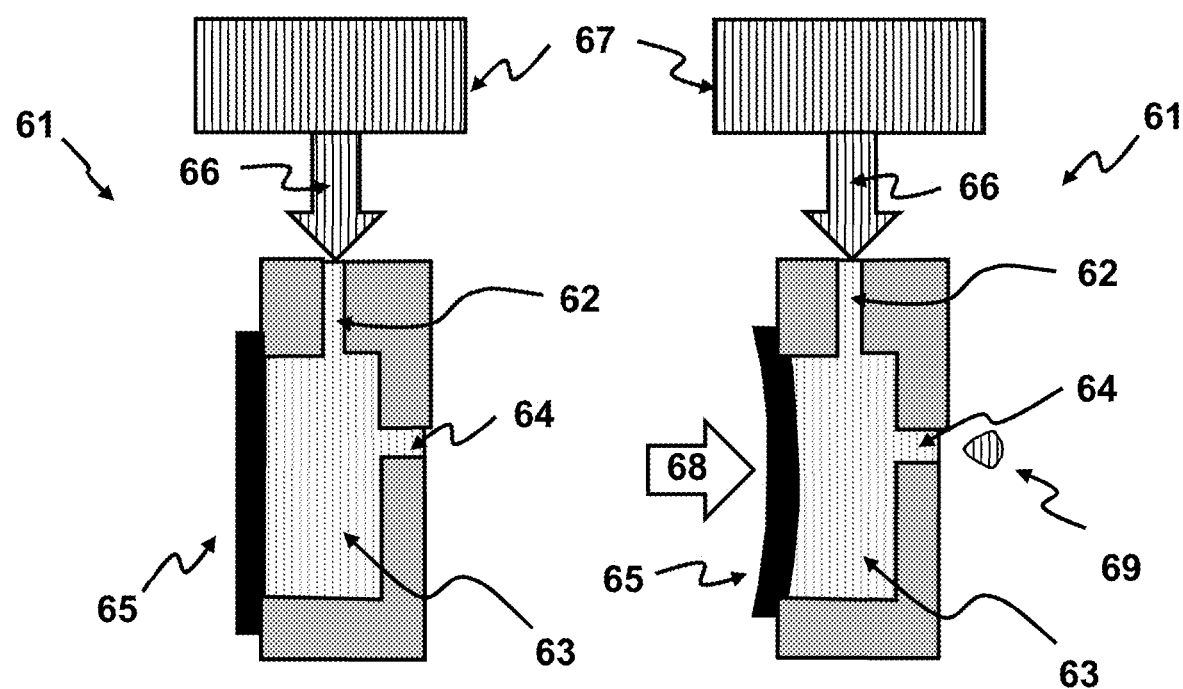
FIG. 6 shows a piezoelectric inkjet (PIJ) dispenser suitable for liquid droplet dispensing by the ADM within the face mask system.

As mentioned above, embodiments of the face mask system 10 could include piezoelectric inkjet (PIJ) dispensers or thermal inkjet (TIJ) dispensers instead of VMN dispensers in some instances. At a high level, PIJ dispensers force liquid droplets from a nozzle by reducing the volume of an adjacent chamber through the application of an electric field to a piezoelectric material. TIJ dispensers, meanwhile, force liquid droplets from a nozzle by heating liquid in an adjacent chamber to boiling, so that a gas bubble is formed that forces a liquid droplet from the nozzle. PIJ and TIJ dispensers are commonly fabricated by photolithographic techniques that are used to pattern and etch physical structures, such as microchannels and microchambers, into silicon. FIG. 6 shows a PIJ dispenser 61 that may be suitable for use in some embodiments. As shown in FIG. 6, the PIJ dispenser 61 comprises a PIJ entrance channel 62, a PIJ dispensing chamber 63, and a PIJ dispensing nozzle 64. Piezoelectric material 65 forms at least a portion of one wall of PIJ dispensing chamber 63. A PIJ liquid 66 to be dispensed flows from PIJ reservoir 67 through PIJ entrance filing channel 62 into PIJ dispensing chamber 63. The piezoelectric material 65 deforms when a suitable voltage is applied by a driver, such as the timer and controller 15 described previously, thereby applying pressure (shown as arrow 68) to the liquid contained within PIJ dispensing chamber 63, resulting in ejection of a droplet 69 of the PIJ liquid 66 through the PIJ dispensing nozzle 64. To keep the PIJ liquid 66 from leaking from PIJ dispensing nozzle 64, the pressure inside the PIJ reservoir 67, PIJ entrance channel 62, and PIJ dispensing chamber 63 customarily are maintained at slightly lower pressure than immediately outside the PIJ dispenser 61, usually by way of a pressure adjustor placed in the PIJ reservoir 67. Further information regarding pressure adjustors can be found in U.S. Pat. No. 4,509,062, titled "Ink Reservoir with Essentially Constant Negative Back Pressure," which is incorporated by reference herein in its entirety.

Advantageously, the energy required to eject a droplet from a PIJ dispenser generally is much smaller than the energy needed to eject a droplet from a comparable TIJ dispenser because the PIJ dispenser does not heat the liquid contained therein. The energy required for dispensing by a PIJ dispenser is largely attributable to the increased kinetic energy of an ejected droplet 69. For aqueous droplets with a volume of about 10 picoliters, that are ejected at a velocity of about 10 m/sec, the kinetic energy is approximately 1 nano-joule. This is roughly 10 times less energy than is required to dispense the same volume of water by a VMN dispenser and roughly 1,000 times less energy than is required to dispense the same volume of water by a TIJ dispenser. Further information regarding PIJ dispensers can be found in U.S. Pat. No. 5,946,012, titled "Reliable High Performance Drop Generator for an Inkjet Printhead," which is incorporated by reference herein in its entirety.

A PIJ dispenser, similar to those manufactured by Dimatix Print Systems for inkjet printing applications, may be suitable for use in embodiments of the face mask system described herein. Generally, PIJ dispensers are configured to eject a droplet of liquid when a voltage in the range of 15 to 50 V is applied to its piezoelectric element. The instantaneous power needed to dispense a 10-picoliter droplet is normally about 1 mW. Available nozzle sizes for PIJ dispensers generally provide for dispensing droplets that range in volume from 1 to 10 picoliters. The dispense speed can be as high as 80 kHz, which reduces the number of nozzles that would be needed in a given face mask system. Simply put, when droplets of liquid can be emitted at high frequencies (e.g., with a PIJ dispenser), a high number of nozzles (e.g., hundreds or thousands) may not be necessary. In contrast, TIJ dispensers generally operate at lower frequencies (e.g., roughly 20 kHZ or less), and therefore more TIJ nozzles will be needed to eject the same number of droplets during an inhalation phase of a respiratory cycle.

Figure 7:
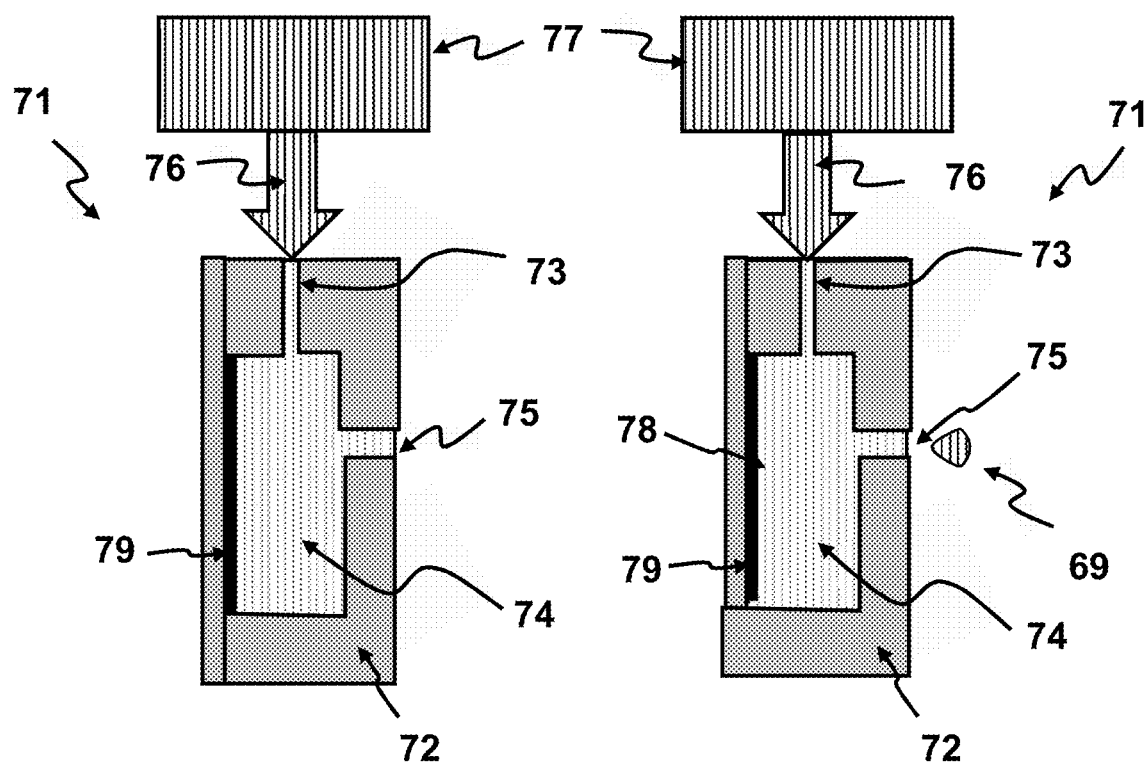
FIG. 7 shows a thermal inkjet (TIJ) dispenser suitable for liquid droplet dispensing by the ADM within the face mask system.

The TIJ dispenser, however, may be suitable as a droplet generator 14 in some embodiments of the face mask system 10. Further information regarding TIJ dispensers can be found in U.S. Pat. No. 4,296,421, titled "Ink Jet Recording Device Using Thermal Propulsion and Mechanical Pressure Changes," and U.S. Pat. No. 4,490,728, titled "Thermal Ink Jet Printer," which are incorporated by reference herein in their entirety. TIJ dispensers are similar to PIJ dispensers but consume considerably more energy as mentioned above. Generally, however, TIJ dispensers are less expensive to manufacture, so TIJ dispensers may be useful in embodiments where cost is relevant. FIG. 7 shows a TIJ dispenser 71 that comprises a silicon substrate 72 with a TIJ entrance channel 73, a TIJ dispensing chamber 74, and a TIJ dispensing nozzle 75. Additionally, a heating resistor 79 is deployed on at least one wall of the TIJ dispensing chamber 74. A TIJ liquid 76 to be dispensed is delivered from a TIJ reservoir 77, through TIJ entrance channel 73, and into the TIJ dispensing chamber 74. A liquid droplet 69 subsequently is dispensed from TIJ dispensing nozzle 75 when a suitable current is applied to heating resistor 79 to create sufficient heat to boil a portion of the liquid in TIJ dispensing chamber 74. The boiling generates a vapor bubble 78 that forces a droplet 69 from TIJ dispensing nozzle 75. Similar to the operation of PIJ dispensers, TIJ reservoir 77, TIJ entrance channel 73, and TIJ dispensing chamber 74 customarily are maintained at slightly lower pressure than immediately outside the TIJ dispenser to keep TIJ dispensing nozzle 75 from leaking the TIJ liquid 76 during periods between droplet dispensing. A pressure adjustor within TIJ reservoir 77 may be used for this purpose.

A TIJ dispenser like those manufactured by Hewlett Packard for inkjet printing applications may be suitable for use in embodiments of the face mask system described herein. As an example, the TIJ dispenser may be similar to the HP45 cartridge that has 300 nozzles with 52 electrical pads, as well as heating resistor values of 40 ohms. Switching transistors can be integrated onto a silicon substrate (also referred to as the "chip"), together with the filling and dispensing channels and heating resistors, so that each resistor is addressable from at least one of the 52 electrical pads. The TIJ dispenser may be able to dispense droplets at frequencies between 1 and 20 kHz. Implementing TIJ dispensers within a face mask system requires special attention to the power and energy that must be supplied by power source 17. Normally, dispensing requires a nominal 12 volt pulse that draws 300 mA of current for 2 microseconds. Therefore, the instantaneous power required is about 3.6 W (300 mA×12 volts), and the energy required for dispensing each 30 picoliter droplet is about 7.2 microjoules (3.6 W×2 microseconds). The total amount of energy needed to dispense the entire aqueous liquid volume from a 36 ml reservoir is about 8.6 kilojoules (7.2 microjoules/30 picoliters×36 ml). A 3-volt CR2 Li-ion rechargeable battery (3 W, 8.6 kJ) that weighs between 10 and 11 grams may be selected as the power source 17 in embodiments where the face mask system includes a TIJ dispenser. The CR2 Li-ion battery may support operation of one nozzle of a TIJ dispenser at a time. Interleaving the operation of several (e.g., between 10 and 50) nozzles, one at a time, can provide for roughly 500,000 30-picoliter droplets to be dispensed over the course of a second.

Figure 8A:
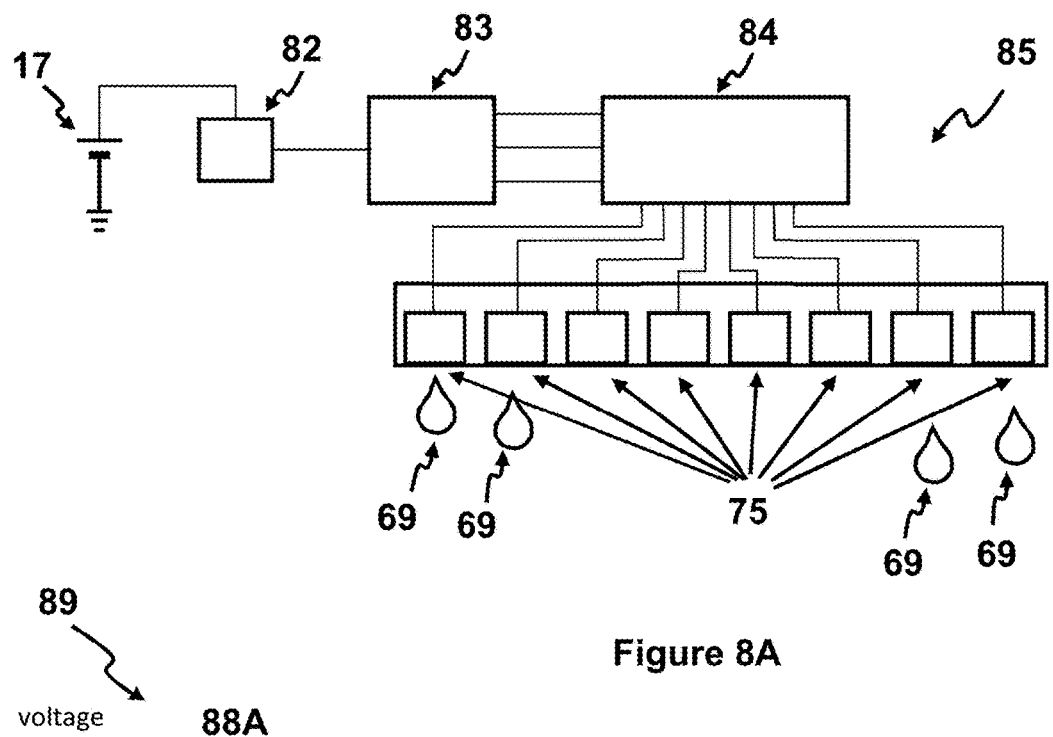
FIG. 8A is a schematic diagram showing a power source, DC-to-DC power converter, microprocessor, and a TIJ dispenser for liquid droplet dispensing by the ADM within the face mask system.

FIG. 8A is a schematic diagram showing power source 17, direct current (DC) voltage converter 82, and a microprocessor 83 for operating a microprocessor-controlled TIJ dispenser 85 in accordance with some embodiments. The power source 17 usually will be a 3.0-3.7 volt rechargeable battery that is connected to a DC-to-DC voltage converter 82 that increases the supply voltage from 3.0-3.7 volts to 12 volts. Suitable DC-to-DC voltage converters are available as miniaturized integrated circuits, for example, the Max1522-1524, Max17291, MAX17250, and MAX1771 DC-to-DC voltage converters manufactured by Maxim Integrated. Also, a MAX17291 DC voltage converter device is available as a wafer-level package that covers 1.27 mm×0.87 mm in area. In the embodiment of the face mask system shown in FIG. 8A, the microprocessor 83 also comprises the timer and controller 15 discussed above. Microprocessor 83 has a multiplicity of electrical outputs, three of which are shown schematically in FIG. 8A, that make separate contact with individual electrical circuits within microprocessor-controlled TIJ dispenser 85 through fifty-two electrical contact pads on an external surface of the TIJ dispenser 85. Each electrical contact pad can address a multiplicity of additional switching transistors 84 that are embedded within the silicon substrate 72 of the microprocessor-controlled TIJ dispenser 85. The switching transistors 84, in turn, can make individual contact to three hundred separate heating resistors of the microprocessor-controlled TIJ dispenser 85 to dispense droplets from any one or more of the three hundred dispensing nozzles 75. Accordingly, the microprocessor 83 can separately control each of the three hundred dispensing nozzles 75 of the microprocessor-controlled TIJ dispenser 85.

Figure 8B:
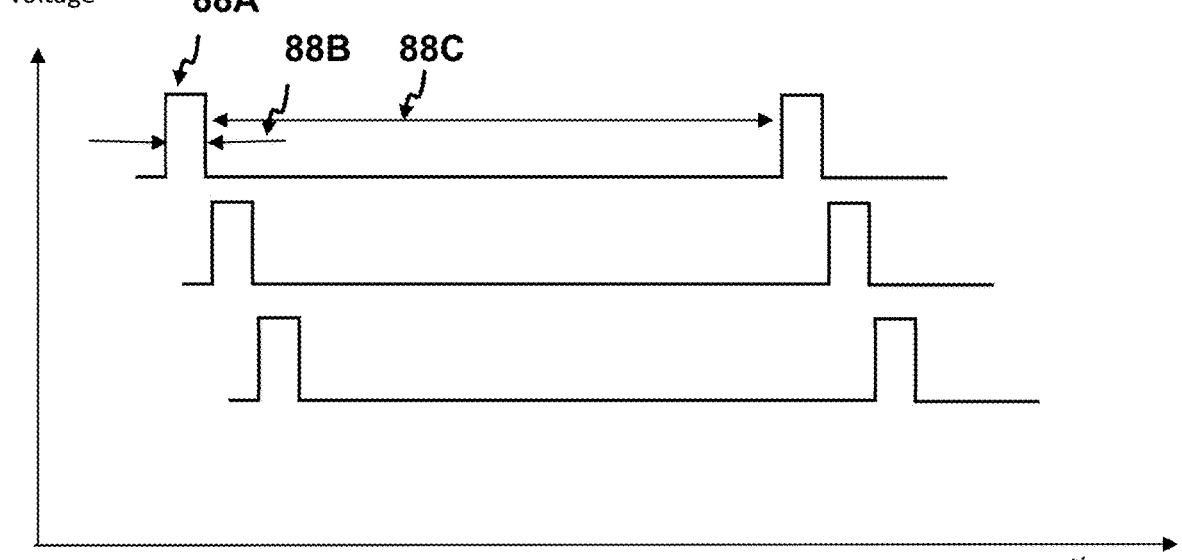
FIG. 8B shows a preferred timing sequence for operating multiple nozzles of a TIJ dispenser, one at a time, when used for liquid droplet dispensing by the ADM within the face mask system.

FIG. 8B shows the time-varying voltage of three representative outputs of microprocessor 83 of FIG. 8A. A dispensing pulse 88A, usually between 12 to 14 volts in amplitude, can cause one droplet to be dispensed at a preselected dispensing nozzle of the three hundred dispensing nozzles 75. The volume of the liquid droplet 69 is predetermined based on the volumes of TIJ dispensing chamber 74, and vapor bubble 78 as shown in FIG. 7. Customarily, the volume of the liquid droplet is less than 1 nanoliter (and more typically between 1 and 50 picoliters). The dispensing pulses 88A are of a predetermined duration, customarily about 2 microseconds, as indicated by 88B in FIG. 8B, but the dispensing pulses 88A may be within a general range of 0.1 to 10 microseconds (and typically less than 5 microseconds). Each dispensing pulse 88A may result in dispensation of a single droplet 69 of liquid from a predetermined dispensing nozzle 75. Dispensation from the same predetermined nozzle 75 can be repeated at a predetermined time interval 88C. For example, at an operating frequency of 10 kHz, the interval 88C between 2 microsecond dispensing pulses 88A may be about 98 microseconds as shown in FIG. 8B.

The three sets of horizontal lines in FIG. 8B, each having two dispensing pulses, represents microprocessor 83 addressing three different individual dispensing nozzles 75 in a staggered way so that no two nozzles dispense at the same time. Such an approach allows the power source 17 that is needed to power the mask system 10 to be minimized by requiring only a maximum power of 3.6 W for operation of a single dispensing nozzle at a time. In this way, up to 50 dispensing nozzles can be operated in sequence at a 10 kHz repeat frequency without overlap, or up to 100 nozzles may be operated in this fashion at a 20 kHz repeat frequency, and so on.

Remarks

The foregoing description of various embodiments of the technology has been provided for the purposes of illustration and description. It is not intended to be exhaustive or to limit the claimed subject matter to the precise forms disclosed.

Many modifications and variations will be apparent to those skilled in the relevant art. Embodiments were chosen and described in order to best describe the principles of the technology and its practical applications, thereby enabling others skilled in the relevant art to understand the claimed subject matter, the various embodiments, and the various modifications that are suited to the particular uses contemplated.

What is claimed is:

1. A self-contained system comprising:
a mask enclosure comprised of breathable fabric that, when worn by a user, is adapted to flexibly conform to the face of the user to form a cavity between the mask enclosure and the face that includes the mouth and nose of the user,
  wherein the mask enclosure comprises outer and inner layers of the breathable fabric, and
  wherein when the mask enclosure is worn by the user, the inner layer defines a periphery of the cavity and the outer layer is exposed to ambient air outside the cavity;
a reservoir in which liquid is stored,
  wherein the reservoir is located in an interstitial region between the outer and inner layers of the mask enclosure and attached to, and supported by, the mask enclosure; and
a dispensing mechanism that includes—
  a sensor configured to generate measurements that are representative of a characteristic of air that is exhaled through the nostrils or mouth of the user,
  a controller configured to generate a signal in response to determining, in real time based on analysis of the measurements, that an exhalation phase has ended, and
  a droplet generator configured to
    initiate, in response to receiving the signal from the controller, dispensation of the liquid from the reservoir into the cavity in the form of droplets that do not exceed one nanoliter in volume,
    wherein dispensation begins when an inhalation phase commences, so as to humidify air drawn into the nostrils or mouth during the inhalation phase, and
    wherein dispensation ends before the inhalation phase concludes, such that dispensation occurs over only an initial portion of the inhalation phase,
  wherein the droplet generator is attached directly to the reservoir without any intervening tubing or channels so that the droplet generator and the reservoir are supported by the mask enclosure.

2. The self-contained system of claim 1, wherein the droplet generator includes
(i) a plate with
  a first side that has one or more ingress holes through which the liquid is able to enter the plate, and
  a second side that has one or more egress holes through which the liquid is able to exit the plate,
  wherein the one or more ingress holes on the first side are fluidly connected to the one or more egress holes on the second side, and
(ii) a vibration element configured to induce movement of the liquid through the plate through ultrasonic vibration.

3. The self-contained system of claim 1,
wherein the sensor is an accelerometer that is connected to a flap situated in an exhaust valve in the breathable fabric of the mask enclosure, and
wherein the accelerometer measures motion of the flap, the motion being indicative of whether air is presently being exhaled through the nostrils or mouth of the user.

4. The self-contained system of claim 1,
wherein the sensor is an accelerometer that is mounted to a flexible membrane embedded in the mask enclosure, and
wherein the accelerometer is configured to generate measurements that are indicative of motion of the flexible membrane.

5. The self-contained system of claim 1,
wherein the sensor is a temperature sensor that is located along an interior surface of the mask enclosure, and
wherein the temperature sensor measures temperature of air inside the cavity of the mask enclosure, the temperature being indicative of whether air is presently being exhaled through the nostrils or mouth of the user.

6. The self-contained system of claim 5, further comprising:
a second temperature sensor that is located along an exterior surface of the mask enclosure,
  wherein the second temperature sensor measures temperature of ambient air outside the cavity of the mask enclosure.

7. The self-contained system of claim 6,
wherein ambient temperature measurements generated by the second temperature sensor are provided to the controller as input, and
wherein the controller is further configured to establish a present phase of a breathing cycle based on a comparison of cavity temperature measurements generated by the temperature sensor and ambient temperature measurements generated by the second temperature sensor.

8. The self-contained system of claim 1,
wherein the droplet generator includes an array of piezoelectric actuators, and
wherein each piezoelectric actuator includes (i) a chamber in which liquid is contained, (ii) a nozzle, and (iii) a piezoelectric element that is configured to displace the liquid in the chamber when a suitable voltage is applied thereto, thereby causing the liquid to be dispensed through the nozzle in the form of a droplet.

9. The self-contained system of claim 1,
wherein the droplet generator includes an array of thermal actuators, and
wherein each thermal actuator includes (i) a chamber in which liquid is contained, (ii) a nozzle, and (iii) a heating element that is configured to heat the liquid to boiling, thereby causing a bubble to form that forces the liquid to be dispensed through the nozzle in the form of a droplet.

10. The self-contained system of claim 9, wherein the thermal actuators in the array are operated sequentially so that droplets are dispensed at a predetermined interval.

11. The self-contained system of claim 10, wherein the predetermined interval is less than 5 microseconds.

12. The self-contained system of claim 1, wherein the mask enclosure includes multiple layers of the breathable fabric so that the droplets substantially are all retained inside the cavity prior to inhalation.

13. The self-contained system of claim 1, further comprising:
a rechargeable power source to which the dispensing mechanism is electrically connected.

14. A self-contained system comprising:
a mask enclosure that, when worn by a user, is adapted to flexibly conform to the face of the user to form a cavity between the mask enclosure and the face of the user,
  wherein the mask enclosure comprises one or more layers of breathable fabric;
a reservoir assembly in which a liquid is stored,
  wherein the reservoir assembly is attached to, and supported by, the mask enclosure;

a sensor configured to generate measurements that are representative of a characteristic of air that is exhaled through the nostrils or mouth of the user;
a controller configured to
monitor a breathing cycle of the user by examining, in real time, the measurements generated by the sensor, and
generate a signal in response to a determination that an exhalation phase of the breathing cycle has ended; and
a droplet generator that is configured to
initiate, in response to receiving the signal from the controller, a programmed sequence for dispensing the liquid from the reservoir, in the form of droplets that are less than 1 nanoliter in volume, into the cavity,
wherein the programmed sequence causes dispensation to occur over an interval of time that corresponds to an initial portion of an inhalation phase, and
wherein the droplet generator is attached directly to the reservoir assembly without any intervening tubing or channels so that the droplet generator and the reservoir are supported by the mask enclosure.

15. The self-contained system of claim 14 wherein the reservoir assembly additionally comprises a concentrated reagent that is separated from the liquid that acts as a diluent.

16. The self-contained system of claim 15, wherein the concentrated reagent comprises equimolar amounts of elemental iodine and iodide anion.

17. The self-contained system of claim 16, wherein upon mixing the concentrated reagent and the liquid, the resulting mixture is a solution comprising between 5 nanomolar and 5 micromolar concentrations of elemental iodine, iodide anion, or tri-iodide anion ($I_3^-$).

18. The self-contained system of claim 14, wherein a volume of liquid stored by the reservoir assembly is no greater than 100 milliliters.

19. The self-contained system of claim 14,
wherein the sensor is an accelerometer that is mounted to a flexible membrane embedded in the mask enclosure,
wherein the flexible membrane is in contact with the cavity, and
wherein the accelerometer monitors motion of the flexible membrane that is caused by reversals in direction of airflow through the nostrils of the user.

20. The self-contained system of 14, wherein the droplet generator includes
(i) a plate with
a first side that has one or more ingress holes through which the mixture is able to enter the plate and
a second side that has one or more egress holes through which the mixture is able to exit the plate,
wherein each ingress hole on the first side is fluidly connected to a corresponding egress hole on the second side, and
(ii) a vibration element configured to induce movement of the mixture through the plate by ultrasonic vibration.

21. The self-contained system of claim 14, wherein a weight of the self-contained system is less than 100 grams.

22. The self-contained system of claim 14, wherein the droplets are dispensed over the interval of time at a frequency of at least 100 kilohertz.

23. A self-contained system comprising:
a mask enclosure comprised of outer and inner fabric layers that, when worn by a user, is adapted to flexibly conform to the face of the user to form a cavity that includes the mouth and nose of the user,
wherein when the mask enclosure is worn by the user, the inner fabric layer defines a periphery of the cavity and the outer fabric layer is exposed to ambient air outside the cavity;
a dispensing mechanism that includes:
(i) a reservoir in which liquid is stored, the reservoir being located in an interstitial region between the outer and inner fabric layers of the mask enclosure,
(ii) a droplet generator that is in direct fluid communication with the reservoir without any intervening tubing or channels,
(iii) a respiratory cycle detector that includes a sensor able to monitor a breathing cycle of the user, and
(iv) a controller that is in electronic communication with the respiratory cycle detector and the droplet generator, and
wherein the dispensing mechanism provides for dispensation of droplets that are less than 1 nanoliter in volume into the cavity in response to measurements made by the sensor of the respiratory cycle detector,
wherein the measurements are representative of a characteristic of air that is exhaled through the mouth or nose of the user, and
wherein dispensation of the droplets begins when an inhalation phase of the breathing cycle of the user commences, so as to humidify air drawn into the mouth or nose during the inhalation phase.

24. The self-contained system of claim 23, wherein the droplet generator includes
(i) a plate with
a first side that has one or more ingress holes through which the liquid is able to enter the plate, and
a second side that has one or more egress holes through which the liquid is able to exit the plate,
wherein the one or more ingress holes on the first side are fluidly connected to the one or more egress holes on the second side, and
(ii) a vibration element configured to induce movement of the liquid through the plate through ultrasonic vibration.

25. The self-contained system of claim 23,
wherein the sensor is an accelerometer that is connected to a flap situated in an exhaust valve in the one or more breathable fabric layers of the mask enclosure, and
wherein the accelerometer measures motion of the flap, the motion being indicative of whether air is presently being exhaled through the mouth or nose of the user.

26. The self-contained system of claim 23,
wherein the sensor is an accelerometer that is mounted to a flexible membrane embedded in the mask enclosure, and
wherein the accelerometer is configured to generate measurements that are indicative of motion of the flexible membrane.

* * * * *